(12) United States Patent
Kim et al.

(10) Patent No.: US 9,540,325 B2
(45) Date of Patent: Jan. 10, 2017

(54) N1-CYCLIC AMINE-N5-SUBSTITUTED PHENYL BIGUANIDE DERIVATIVES, METHODS OF PREPARING THE SAME AND PHARMACEUTICAL COMPOSITION COMPRISING THE SAME

(75) Inventors: Sung Wuk Kim, Seongnam-si (KR); Chang Hee Min, Seoul (KR); Se Hwan Park, Daejeon (KR); Duck Kim, Daegu (KR); Ji Sun Lee, Daejeon (KR); Yong Eun Kim, Daejeon (KR); Ju Hoon Oh, Gangneung-Si (KR)

(73) Assignee: Immunomet Therapeutics, Inc., Cambridge, MA (US)

( * ) Notice: Subject to any disclaimer, the term of this patent is extended or adjusted under 35 U.S.C. 154(b) by 0 days.

(21) Appl. No.: 14/237,514

(22) PCT Filed: Aug. 8, 2012

(86) PCT No.: PCT/KR2012/006326
§ 371 (c)(1),
(2), (4) Date: Feb. 6, 2014

(87) PCT Pub. No.: WO2013/022278
PCT Pub. Date: Feb. 14, 2013

(65) Prior Publication Data
US 2014/0179660 A1 Jun. 26, 2014

(30) Foreign Application Priority Data

Aug. 8, 2011 (KR) .................. 10-2011-0078764
Sep. 2, 2011 (KR) .................. 10-2011-0089272

(51) Int. Cl.
| C07D 295/13 | (2006.01) |
| C07D 211/14 | (2006.01) |
| C07D 205/04 | (2006.01) |
| C07D 207/06 | (2006.01) |
| C07D 223/04 | (2006.01) |
| C07D 257/04 | (2006.01) |
| C07D 295/14 | (2006.01) |

(52) U.S. Cl.
CPC .......... *C07D 211/14* (2013.01); *C07D 205/04* (2013.01); *C07D 207/06* (2013.01); *C07D 223/04* (2013.01); *C07D 257/04* (2013.01); *C07D 295/14* (2013.01)

(58) Field of Classification Search
CPC .................................................. C07D 295/13
USPC ......................................................... 548/569
See application file for complete search history.

(56) References Cited

U.S. PATENT DOCUMENTS 2,467,371 A 4/1949 Curd et al.
3,960,949 A 6/1976 Ahrens et al.

FOREIGN PATENT DOCUMENTS

| CN | 1846694 A | 10/2006 |
| GB | 599714 A | 3/1948 |
| GB | 1198690 A | 7/1970 |
| JP | 2006-523668 A | 10/2006 |
| KR | 102003002905 A | 4/2003 |
| KR | 20110081093 A | 7/2011 |
| WO | WO-2009113092 A2 | 9/2009 |

OTHER PUBLICATIONS

Ainley, A. D. et al. "Synthetic Antimalarials. XXXIII. An Alternative Route to N1-aryl-N5-Alkylbiguanides and Related Compounds: the Condensation of Guanidines and Cyanamides." *Journal of the Chemical Society*. (1949):98-106.
Bami, H. L. and Guha, P.C. "Studies in Antimalarials. IX. N1-Aryl-N5-alkylbiguanides." *Journal of the Indian Institute of Science*. vol. 31A No. Part 1 (1949):1-7.
Clark, R. J. et al. "Derivatives of 3: 4-Xylidine and Related Compounds as Inhibitors of Influenza Virus: Relationships Between Chemical Structure and Biological Activity." *British Journal of Pharmacology and Chemotherapy*. vol. 13 (1958):424-435.
Corbellini, A. et al. "Studies on the antitumoral activity of biguanide compounds." Archivio Italiano di Patologia e Clinica dei Tumori. vol. 8, No. 3-4 (1965):245-257. [English language summary on p. 257].
Curd, F. H. S. and Rose, F.L. "Synthetic antimalarials. Part X. Some Aryl-diguanide ("-biguanide") Derivatives." *Journal of the Chemical Society*. (1947):729-737.
James, John W. et al. "Synthesis of Some Heterocyclic Derivatives of Biguanide with Antibacterial Activity." *Journal of Medicinal Chemistry*. vol. 11, No. 5 (1968):942-945.
Pan, Jin-ping and Fan, Hi-ping. "Synthesis and properties of o-tolylbiguanide." Academic Paper. (2010):040-044. [English language abstract on p. 044].

(Continued)

*Primary Examiner* — Nyeemah A Grazier
(74) *Attorney, Agent, or Firm* — Mintz Levin Cohn Ferris Glovsky and Popeo, P.C.; Fred C. Hernandez; Linyu L. Mitra

(57) ABSTRACT

An N1-cyclic amine-N5-substituted phenyl biguanide derivative of Formula 1 or a pharmaceutically acceptable salt thereof, a method of manufacturing the same, and a pharmaceutical composition including the biguanide derivative or the pharmaceutically acceptable salt thereof as an active ingredient are provided. The biguanide derivatives have an effect of inhibiting cancer cell proliferation and also exhibit anticancer activity including inhibition of cancer metastasis and cancer recurrence, because they are effective in activating AMPK, which is associated with the control of energy metabolism, even when administered in a small dose compared with conventional drugs. Also, the biguanide derivatives are highly effective at lowering blood glucose and lipid concentration by AMPK activation, thus they may be effectively used to treat diabetes mellitus, obesity, hyperlipemia, hypercholesterolemia, fatty liver, coronary artery disease, osteoporosis, polycystic ovary syndrome and metabolic syndrome.

22 Claims, 1 Drawing Sheet

(56) References Cited

OTHER PUBLICATIONS

Rikimaru, Mitsuo. "Relation Between Tissue Culture Cytotoxicity and Acute Toxicity in Mice of Biguanide Derivatives." *Journal of Antibiotics, Series A*.vol. 18, No. 4 (1965):196-199.
Sharma, M. et al. "Piperazino Biguanides as Cysticidal Agents." *Indian Journal of Pharmacy*. vol. 39, No. 5 (1977):113-114.
Yuki, Yasuo et al. "Thermodynamics of Polymerization of 2-Anilno-4-(disubstituted amino)-6-isopropenyl-1, 3, 5-triazines by Means of Differential Scanning Calorimeter." *Bulletin of the Chemical Society of Japan*. vol. No. 12 (1983):1806-1813.
Zakikhani et al. "Metformin is an AMP Kinase-Dependent Growth Inhibitor for Breast Cancer Cells." *Cancer Res*. 66(2006):10269-10273.

N1-CYCLIC AMINE-N5-SUBSTITUTED PHENYL BIGUANIDE DERIVATIVES, METHODS OF PREPARING THE SAME AND PHARMACEUTICAL COMPOSITION COMPRISING THE SAME

CROSS-REFERENCE TO RELATED APPLICATIONS

This application is a national stage application, filed under 35 U.S.C. §371, of International Application No. PCT/KR2012/006326, filed Aug. 8, 2012, which claims priority to and the benefit of Korean Patent Application No. 10-2011-0089272, filed Sep. 2, 2011, and Korean Patent Application No. 10-2011-0078764, filed Aug. 8, 2011, the contents of each of which are incorporated herein by reference in their entireties.

TECHNICAL FIELD

The present invention relates to an N1-cyclic amine-N-5-substituted phenyl biguanide derivative that inhibits cancer cell proliferation, cancer metastasis and cancer recurrence and exhibits excellent effects in treatment of diabetes mellitus and metabolic diseases by activation of 5'-AMP-activated protein kinase (AMPK), even when administered in a small dose compared with conventional drugs, a method of preparing the same, and a pharmaceutical composition comprising the N1-cyclic amine-N5-substituted phenyl biguanide derivative as an active ingredient.

BACKGROUND ART

AMPK is an enzyme that functions to control a metabolic pathway so as to maintain balance between supply of nutrients and demand for energy, and thus maintain energy homeostasis in cells and the whole body. AMPK is activated as the ratio of AMP/ATP in the cells increases due to a hypoxemic state or glucose deficiency. The activated AMPK induces fatty acid oxidation to produce a larger amount of ATP and inhibits anabolisms requiring the use of ATP. Also, AMPK activation enhances sensitivity to insulin, inhibits glucose generation in the liver, and improves glucose absorption in the muscles. Due to its actions, AMPK has been regarded as a desirable target for treatment of type II diabetes mellitus and metabolic diseases. AMPK inhibits proliferation of cancer cells and kills cancer cells by regulating energy metabolism in the cancer cells as well as in normal cells. AMPK activated in cancer cells shows an anticancer activity by phosphorylating mTORC1, p53, fatty acid synthase and the like to regulate the cell cycle, cell polarity, autophagy, apoptosis, etc.

Metformin has been used to treat insulin-independent diabetes mellitus (i.e., type II diabetes mellitus) since it is most effective at lowering blood glucose, does not develop hypoglycemia or hyperinsulinemia and can prevent complications among oral therapeutic agents for treating diabetes mellitus. In recent years, metformin has been extensively researched. Also, it was reported that metformin activates AMP-activated protein kinase (AMPK) by inhibiting the action of complex 1 of the electron transport system in the mitochondria to obstruct intracellular generation of energy and inhibits activation of the mTOR/S6K1 signaling pathway in which proteins essential for survival are produced to obstruct proliferation of cancer cells and tumor growth (Mol. Cancer. Ther. 9(5): 1092-1099 (2010)). Consequently, metformin has received considerable attention as an anticancer agent for regulating cancer cell metabolism. Also, an epidemiological survey confirmed that the incidence of cancer and mortality by cancer were lowered for patients treated with metformin (BMJ. 330: 1304-1305 (2005)).

Meanwhile, there is increasing clinical evidence indicating that cancer stem cells take part in recurrence and metastasis of cancer. The cancer stem cells refer to cancer cells that have self-regeneration or differentiation capacity which is characteristically innate to stem cells. The cancer stem cells are present in the cancer tissue at a content of 0.2% or less, and are characterized by their slow proliferation. Since lots of anticancer agents developed so far target cancer cells that proliferate rapidly, the cancer stem cells are resistant to conventional anticancer therapy when cancer stem cells, are treated with the anticancer agents, thereby causing poor prognoses. On the other hand, it was reported that metformin prevents the recurrence of cancer as it selectively acts on cancer stem cells among breast cancer cells and removes the cancer stem cells (Cancer Res. 69(19): 7507-11 (2009)). Also, it was found that metformin prevents the metastasis of cancer by interfering with the motility and invasion of the cancer cells since it inhibits the expression of Snail1, Slug, Twist, ZEB1/2 and TGF-b, which are transcription factors associated with the epithelial-to-mesenchymal transition (EMT), and promotes the expression of E-cadherin to prevent cancer cells from leading to the EMT (Cell Cycle 10: 7, 1144-1151 (2011), Cell Cycle 9: 18, 3807-3814 (2010), Cell Cycle 9: 22, 4461-4468 (2010)).

However, metformin is generally administered three times a day, with a single dose of approximately 500 mg or more. Thus, a tablet that can contain approximately 1,500 mg or more of metformin is required in order to prepare metformin in the form of a sustained released tablet to be administered once a day. In this case, the tablet is too large for patients to swallow. In addition, since one tablet of a sustained-release preparation currently available on the market contains only approximately 750 mg of metformin, two or more tablets of the sustained-release preparation should be taken. Also, the use of phenformin, which belongs to the same group of biguanides, has been completely prohibited since the late 1970s due to its severe side effects such as lactic acidosis.

For these reasons, there is a need for a biguanide-based substance that exhibits better pharmacological action than the conventional metformin and has improved physiochemical properties without the side effects of phenformin.

DISCLOSURE OF INVENTION

Technical Problem

The present invention is directed to providing a novel biguanide derivative that is highly effective in inhibiting proliferation of cancer cells, cancer metastasis and cancer recurrence, even when administered in a small dose compared with conventional drugs, or a pharmaceutically acceptable salt thereof, and a method of preparing the same.

Also, the present invention is directed to providing a pharmaceutical composition including the above-mentioned compound as an active ingredient that is highly effective at lowering blood glucose and lipid concentration so as to prevent or treat diabetes mellitus, obesity, hyperlipemia, fatty liver, hypercholesterolemia, a coronary artery disease, osteoporosis, polycystic ovary syndrome, metabolic syndrome, etc.

Solution to Problem

One aspect of the present invention provides an N1-cyclic amine-N5-substituted phenyl biguanide derivative compound of Formula 1, or a pharmaceutically acceptable salt thereof:

[Formula 1]

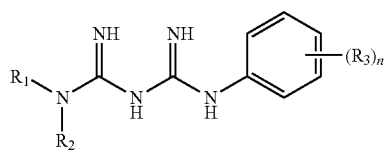

In Formula 1, $R_1$ and $R_2$ are taken together with nitrogen to which they are attached to form 3- to 8-membered heterocycloalkyl;

n is an integer ranging from 0 to 5;

when there is more than one $R_3$, each $R_3$ is independently selected from the group consisting of hydrogen, halogen, hydroxy, $C_{1-6}$alkyl, $C_{1-6}$alkoxy, $C_{1-6}$alkylthio, amino, amide, sulfonamide, nitro, heteroaryl, cyano, sulfonic acid and sulfamoyl; and $R_1$ and $R_2$, or $R_3$ are each independently unsubstituted or substituted with at least one substituent selected from the group consisting of halogen, hydroxy and $C_{1-6}$alkyl.

In this specification, a "substituted" group refers to a group in which at least one hydrogen atom is replaced with at least one non-hydrogen atom group, provided that the group satisfies the valence electron requirements and forms a chemically stable compound from the substitution. Unless explicitly described as "unsubstituted" in this specification, it should be understood that all substituents will be unsubstituted or substituted with another substituent. The substituents $R_1$ to $R_3$ on the biguanide derivative according to the present invention may each be re-substituted with at least one of the above-defined substituents.

The term "halogen" or "halo" refers to fluoro, chloro, bromo, and iodo.

The term "hydroxy" refers to —OH.

The term "alkyl" refers to a linear and branched saturated hydrocarbon group generally having a specified number of carbon atoms (for example, 1 to 12 carbon atoms). Examples of the alkyl group include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth1-yl, n-hexyl, n-heptyl and n-octyl. The alkyl may be attached to a parent group or a substrate at any ring atom, unless the attachment would violate valence electron requirements. Likewise, the alkyl group may include at least one non-hydrogen substituent unless the substitution would violate valence electron requirements. For example, the term "haloalkyl" refers to a group such as —CH$_2$(halo), —CH(halo)$_2$ or C(halo)$_3$, meaning a methyl group in which at least one hydrogen atom is replaced with halogen. Examples of the term "haloalkyl" group include, without limitation, trifluoromethyl, trichloromethyl, tribromomethyl and triiodomethyl.

The term "alkoxy" refers to alkyl-O—, provided that the alkyl is the same as defined above. Examples of the alkoxy group include, without limitation, methoxy, ethoxy, n-propoxy, i-propoxy, n-butoxy, s-butoxy, t-butoxy, n-pentoxy, s-pentoxy, etc. The alkoxy may be attached to a parent group or a substrate at any ring atom, unless the attachment would violate valence electron requirements. Likewise, the alkoxy group may include at least one non-hydrogen substituent unless the attachment would violate valence electron requirements. For example, the term "haloalkoxy" refers to —O—CH$_2$ (halo), —O—CH(halo)$_2$ or —O—C(halo)$_3$, meaning a methyl group in which at least one hydrogen atom is replaced with halogen. Examples of the term "haloalkoxy" group include, without limitation, trifluoromethoxy, trichloromethoxy, tribromomethoxy and triiodomethoxy.

The term "alkylthio" refers to alkyl-S—, provided that the alkyl is the same as defined above. Examples of the alkylthio group include, without limitation, methylthio, ethylthio, n-propylthio, i-propylthio, n-butylthio, s-butylthio, t-butylthio, n-pentylthio, s-pentylthio, etc. The alkylthio group may be attached to a parent group or a substrate at any ring atom, unless the attachment would violate valence electron requirements. Likewise, the alkylthio group may include at least one non-hydrogen substituent unless the attachment would violate valence electron requirements.

The term "cycloalkyl" refers to a saturated monocyclic and dicyclic hydrocarbon ring generally having the specified number of carbon atoms that include a ring (for example, $C_{3-8}$cycloalkyl refers to a cycloalkyl group having 3, 4, 5, 6, 7 or 8 carbon atoms as a ring member). The cycloalkyl may be attached to a parent or substrate at any ring atom, unless the attachment would violate valence electron requirements. Likewise, the cycloalkyl group may include at least one non-hydrogen substituent unless the substitution would violate valence electron requirements. The term "heterocycloalkyl" refers to a monocyclic and dicyclic hydrocarbon ring having 3 to 12-membered ring atoms containing 1 to 3 heteroatoms independently selected from nitrogen, oxygen and sulfur. The heterocycloalkyl may be attached to a parent or substrate at any ring atom, unless the attachment would violate valence electron requirements. Likewise, the heterocycloalkyl group may include at least one non-hydrogen substituent unless the substitution would violate valence electron requirements. Examples of the heterocycloalkyl group include, without limitation, aziridine, azetidine, imidazolyl, pyrrolyl, pyrrolidinyl, piperidyl, morpholinyl, piperazinyl, azepanyl, indolyl, indolinyl, etc.

The term "amino" refers to a —NH$_2$ group. The "amino" group may include at least one non-hydrogen substituent unless the substitution would violate valence electron requirements. For example, the term "dialkylamino" refers to —N(alkyl)$_2$, provided that the alkyl is the same as defined above. Examples of the "dialkylamino" include, without limitation, dimethylamine, diethylamine, dipropylamine and dibutylamine.

The term "amide" refers to —NH—C(O)—R'. Here, the residue R' represents a lower alkyl having 1 to 6 carbon atoms. Examples of the "amide" group include, without limitation, acetamide, propanamide and butanamide.

The term "sulfonamide" refers to —NH—S(O)$_2$—R', provided that the residue R' represents, for example, a lower alkyl having 1 to 6 carbon atoms. Examples of the "sulfonamide" group include, without limitation, methylsulfonamide.

The term "aryl" refers to monovalent and bivalent aromatic groups, respectively including 5- and 6-membered monocyclic aromatic groups and "heteroaryl" refers to monovalent and bivalent aromatic groups, respectively including 5- and 6-membered monocyclic aromatic groups that contain 1 to 4 heteroatoms independently selected from nitrogen, oxygen and sulfur. Examples of the "heteroaryl" group include, without limitation, furanyl, pyrrolyl, thiopheneyl, thiazolyl, isothiazolyl, imidazolyl, triazolyl, tetrazolyl, pyrazolyl, oxazolyl, isooxazolyl, pyrazinyl, pyrazinyl, pyridazinyl, pyrimidinyl, isoquinolinyl, carbazolyl, benzoxazolyl, benzodioxazolyl, benzothiazolyl, benzimidazolyl, benzothiophenyl, triazinyl, phthalazinyl, quinolinyl, indolyl, benzofuranyl, furinyl and indolizinyl.

The term "sulfamoyl" refers to —S(O)$_2$—NH$_2$, and the term "sulfonicacid" refers to —S(O)$_2$—OH.

According to one exemplary embodiment, $R_1$ and $R_2$ are taken together with nitrogen to which they are attached to form 4- to 7-membered heterocycloalkyl;

n is an integer ranging from 0 to 5;

when there is more than one $R_3$, each $R_3$ is independently selected from the group consisting of hydrogen, halogen, hydroxy, $C_{1-6}$alkyl, $C_{1-6}$alkoxy, $C_{1-6}$alkylthio, amino, amide, sulfonamide, nitro, heteroaryl, cyano, sulfonic acid and sulfamoyl; and $R_1$ and $R_2$, or $R_3$ are each independently unsubstituted or substituted with at least one substituent selected from the group consisting of halogen, hydroxy and $C_{1-6}$alkyl.

According to one exemplary embodiment, $R_1$ and $R_2$ may be taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl;

n may be an integer ranging from 0 to 5;

when there is more than one $R_3$, each $R_3$ may be independently selected from the group consisting of hydrogen, halogen, hydroxy, $C_{1-6}$alkyl, $C_{1-6}$alkoxy, $C_{1-6}$alkylthio, amino, amide, sulfonamide, nitro, heteroaryl, cyano, sulfonic acid and sulfamoyl; and $R_1$ and $R_2$, or $R_3$ may each be independently unsubstituted or substituted with at least one substituent selected from the group consisting of halogen, hydroxy and $C_{1-6}$alkyl.

According to another exemplary embodiment, $R_1$ and $R_2$ may be taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl;

n may be an integer ranging from 0 to 3;

when there is more than one $R_3$, each $R_3$ may be independently selected from the group consisting of hydrogen, halogen, hydroxy, $C_{1-6}$alkyl, $C_{1-6}$alkoxy, $C_{1-6}$alkylthio, amino, amide, sulfonamide, nitro, heteroaryl, cyano, sulfonic acid and sulfamoyl; and $R_1$ and $R_2$, or $R_3$ may each be independently unsubstituted or substituted with at least one substituent selected from the group consisting of halogen, hydroxy and $C_{1-6}$alkyl.

According to still another exemplary embodiment, $R_1$ and $R_2$ may be taken together with nitrogen to which they are attached to form 4- to 7-membered heterocycloalkyl selected from the group consisting of azetidinyl, pyrrolidinyl, piperidinyl, morpholinyl, piperazinyl and azepanyl;

n may be an integer ranging from 0 to 3;

when there is more than one $R_3$, each $R_3$ may be independently selected from the group consisting of hydrogen, halogen, hydroxy, $C_{1-6}$alkyl, $C_{1-6}$alkoxy, $C_{1-6}$alkylthio, amino, amide, sulfonamide, heteroaryl, sulfonic acid and sulfamoyl; and $R_1$ and $R_2$, or $R_3$ may each be independently unsubstituted or substituted with at least one substituent selected from the group consisting of halogen, hydroxy and $C_{1-6}$alkyl.

According to still another exemplary embodiment, $R_1$ and $R_2$ may be taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl, provided that the piperazinyl is substituted with $C_{1-6}$alkyl;

n may be an integer ranging from 0 to 3; and when there is more than one $R_3$, each $R_3$ may be independently selected from the group consisting of hydrogen, halogen, hydroxy, $C_{1-6}$alkyl, $C_{1-6}$alkoxy, $C_{1-6}$alkylthio, amino, amide, sulfonamide, nitro, heteroaryl, cyano, sulfonic acid and sulfamoyl, provided that the $C_{1-6}$alkyl or $C_{1-6}$alkoxy may be each independently substituted with halogen or hydroxy, the amino may be unsubstituted or substituted with $C_{1-6}$alkyl, the amide may be acetamide, the sulfonamide may be alkylsulfonamide, and the heteroaryl may be tetrazolyl.

According to yet another exemplary embodiment, $R_1$ and $R_2$ may be taken together with nitrogen to which they are attached to form pyrrolidinyl or piperidinyl;

n may be 1 or 2; and when there is more than one $R_3$, each $R_3$ may be independently selected from the group consisting of hydrogen, halogen, haloalkyl and haloalkoxy.

According to one exemplary embodiment, the compound of Formula 1 may be

N1-piperidine-N5-(3-bromo)phenyl biguanide; N1-piperidine-N5-phenyl biguanide;

N1-piperidine-N5-(3-methyl)phenyl biguanide; N1-piperidine-N5-(3-ethyl)phenyl biguanide; N1-piperidine-N5-(3-hydroxy)phenyl biguanide;

N1-piperidine-N5-(3-hydroxymethyl)phenyl biguanide;

N1-piperidine-N5-(3-methoxy)phenyl biguanide; N1-piperidine-N5-(4-fluoro)phenyl biguanide; N1-piperidine-N5-(2-fluoro)phenyl biguanide;

N1-piperidine-N5-(3-fluoro)phenyl biguanide; N1-pyrrolidine-N5-(4-chloro)phenyl biguanide; N1-piperidine-N5-(4-chloro)phenyl biguanide;

N1-pyrrolidine-N5-(3-chloro)phenyl biguanide; N1-piperidine-N5-(3-chloro)phenyl biguanide; N1-azepane-N5-(3-chloro)phenyl biguanide;

N1-morpholine-N5-(3-bromo)phenyl biguanide;

N1-pyrrolidine-N5-(3-trifluoromethyl)phenyl biguanide;

N1-piperidine-N5-(3-trifluoromethyl)phenyl biguanide;

N1-azetidine-N5-(4-trifluoromethyl)phenyl biguanide;

N1-pyrrolidine-N5-(4-trifluoromethyl)phenyl biguanide;

N1-piperidine-N5-(4-trifluoromethyl)phenyl biguanide;

N1-pyrrolidine-N5-(3-trifluoromethoxy)phenyl biguanide;

N1-piperidine-N5-(3-trifluoromethoxy)phenyl biguanide;

N1-piperidine-N5-(3-difluoromethoxy)phenyl biguanide;

N1-azetidine-N5-(4-trifluoromethoxy)phenyl biguanide;

N1-pyrrolidine-N5-(4-trifluoromethoxy)phenyl biguanide;

N1-piperidine-N5-(4-trifluoromethoxy)phenyl biguanide;

N1-morpholine-N5-(4-trifluoromethoxy)phenyl biguanide;

N1-(4-methyl)piperazine-N5-(4-trifluoromethoxy)phenyl biguanide;

N1-piperidine-N5-(3-amino)phenyl biguanide;

N1-piperidine-N5-(4-dimethylamino)phenyl biguanide;

N1-piperidine-N5-(4-acetamide)phenyl biguanide;

N1-piperidine-N5-(3-acetamide)phenyl biguanide; N1-piperidine-N5-(4-(1H-tetrazole-5-yl))phenyl biguanide; N1-piperidine-N5-(3-methylsulfonamide)phenyl biguanide; N1-piperidine-N5-(4-sulfonicacid)phenyl biguanide;

N1-piperidine-N5-(4-methylthio)phenyl biguanide;

N1-piperidine-N5-(4-sulfamoyl)phenyl biguanide;

N1-piperidine-N5-(3,5-dimethoxy)phenyl biguanide;

N1-piperidine-N5-(4-fluoro-3-trifluoromethyl)phenyl biguanide;

N1-piperidine-N5-(4-chloro-3-trifluoromethyl)phenyl biguanide;
N1-pyrrolidine-N5-(3-fluoro-4-trifluoromethyl)phenyl biguanide;
N1-piperidine-N5-(3-fluoro-4-trifluoromethyl)phenyl biguanide;
N1-piperidine-N5-(4-fluoro-3-trifluoromethoxy)phenyl biguanide;
N1-piperidine-N5-(4-chloro-3-trifluoromethoxy)phenyl biguanide;
N1-azetidine-N5-(3-fluoro-4-trifluoromethoxy)phenyl biguanide;
N1-pyrrolidine-N5-(3-fluoro-4-trifluoromethoxy)phenyl biguanide;
N1-piperidine-N5-(3-fluoro-4-trifluoromethoxy)phenyl biguanide;
N1-azetidine-N5-(3-chloro-4-trifluoromethoxy)phenyl biguanide;
N1-pyrrolidine-N5-(3-chloro-4-trifluoromethoxy)phenyl biguanide;
N1-piperidine-N5-(3-chloro-4-trifluoromethoxy)phenyl biguanide;
N1-piperidine-N5-(2,4-difluoro)phenyl biguanide;
N1-piperidine-N5-(3,4-difluoro)phenyl biguanide;
N1-piperidine-N5-(3,5-difluoro)phenyl biguanide;
N1-piperidine-N5-(3,5-dichloro)phenyl biguanide;
N1-piperidine-N5-(2,4-dichloro)phenyl biguanide;
N1-pyrrolidine-N5-(3,4-dichloro)phenyl biguanide;
N1-piperidine-N5-(3,4-dichloro)phenyl biguanide;
N1-piperidine-N5-(3-chloro-5-trifluoromethoxy)phenyl biguanide;
N1-pyrrolidine-N5-(3-bromo-5-trifluoromethoxy)phenyl biguanide;
N1-piperidine-N5-(3-bromo-5-trifluoromethoxy)phenyl biguanide;
N1-piperidine-N5-(3,4,5-trifluoro)phenyl biguanide; or
N1-piperidine-N5-(2,4,6-trifluoro)phenyl biguanide.

Meanwhile, a pharmaceutically acceptable salt of the compound of Formula 1 according to the present invention may be an acid addition salt formed using an organic acid or an inorganic acid. For example, the organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzensulfonic acid, 4-toluenesulfonic acid and methanesulfonic acid; and the inorganic acid may include, for example, hydrochloric acid, hydrobromic acid, sulfuric acid, phosphoric acid, nitric acid, carbonic acid and boric acid. For example, the above-described acid addition salt may be prepared by a typical method of preparing a salt, including a) directly mixing the compound of Formula 1 and an acid, b) dissolving one of the compounds and an acid in a solvent or a hydrated solvent and mixing the resulting solution with the other element, or c) dissolving the compound of Formula 1 and an acid in a solvent or hydrated solvent, respectively, and mixing them.

According to one exemplary embodiment, the pharmaceutically acceptable salt of the compound of Formula 1 may be a salt of an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid. According to one exemplary embodiment of the present invention, the acetate of the compound of Formula 1 may be provided as one example of the pharmaceutically acceptable salt of the compound of Formula 1. The acetate of the compound of Formula 1 shows remarkably high solubility and more desirable or identical pharmacological effects, compared with the hydrochloride salt of the compound of Formula 1.

The compound of Formula 1 according to the present invention may be prepared by a number of methods.

According to one exemplary embodiment, there is a method of preparing a compound of Formula 1, which includes reacting a compound of Formula 2 with dicyanoamide in at least one organic solvent to obtain a compound of Formula 3; and reacting the compound of Formula 3 with a compound of Formula 4 in at least one organic solvent to obtain the compound of Formula 1:

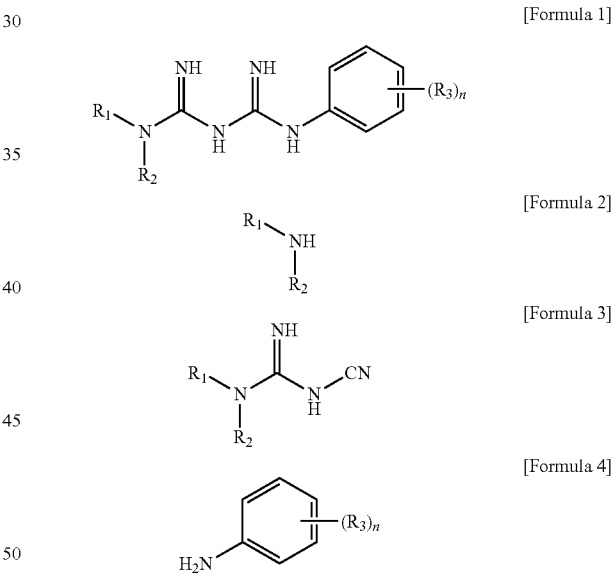

In Formula 1 to 4, $R_1$, $R_2$, $R_3$ and n are the same as defined in Formula 1.

For example, the preparation method may be illustrated in the following Scheme 1, and will be described by operations, as follows.

Scheme 1

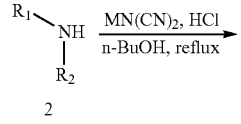

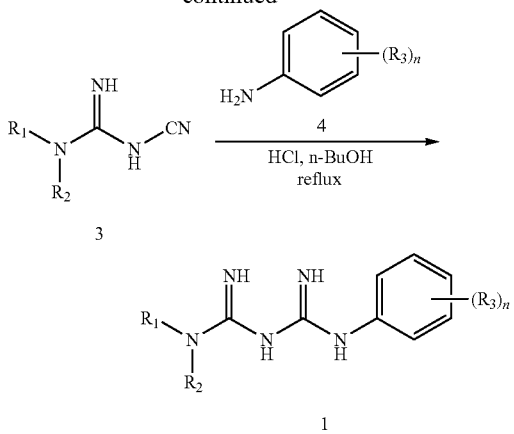

M = Na or K

In the method of preparing the compound of Formula 1, the cyanoguanidine compound of Formula 3 used as an intermediate may be obtained by reacting the cyclic amine of Formula 2 with a dicyanoamide such as sodium or potassium dicyanoamide in at least one organic solvent, in the presence of an acid. Then, the compound of Formula 1 may be obtained by refluxing the obtained cyanoguanidine compound of Formula 3 with the compound of Formula 4 in water, at least one organic solvent or a mixture thereof.

An amount of the dicyanoamide used for preparation of the cyanoguanidine compound of Formula 3 is equivalent to approximately 1 to 3 moles with respect to the compound of Formula 2, an amount of the acid (for example, hydrochloric acid, sulfuric acid, nitric acid, hydrobromic acid, 4-toluenesulfonic acid, etc.) is equivalent to approximately 1 to 2 moles with respect to the compound of Formula 2, and methanol, ethanol, propanol, butanol, pentanol, acetonitrile, benzene, toluene, 1,4-dioxane or N,N-dimethylamide may be used as the organic solvent. The reaction temperature is in the range of 60 to 140° C., and the reaction time is in the range of 3 to 24 hours.

After the cyanoguanidine compound of Formula 3 obtained above is dissolved in water, an organic solvent (i.e., methanol, ethanol, propanol, butanol, pentanol, acetonitrile, benzene, toluene, 1,4-dioxane, N,N-dimethylamide, etc.) or a mixture thereof, the compound of Formula 4 and an acid (i.e., hydrochloric acid, sulfuric acid, nitric acid, hydrobromic acid, 4-toluenesulfonic acid, etc.) are added, and then stirred under reflux. Here, an amount of the compound of Formula 4 is equivalent to approximately 1 to 2 moles with respect to the compound of Formula 3, and an amount of the acid is equivalent to approximately 1 to 2 moles with respect to the compound of Formula 3. The reaction temperature is in the range of the reflux temperature of the solvent used (i.e., 120 to 140° C. for butanol), and the reaction time is in the range of 6 to 24 hours. When the reaction is completed, the resulting reaction solution is filtered. Thereafter, the pH of the filtered reaction solution may then be controlled to approximately 4 to 5 using an acid such as hydrochloric acid. Then, the resulting solution may be concentrated and purified to yield the compound of Formula 1 or a pharmaceutically acceptable salt thereof according to the present invention.

The compound of Formula 1 or the pharmaceutically acceptable salt thereof produced in this way may exhibit anticancer activity including inhibition of cancer metastasis and cancer recurrence, and may also have an effect in lowering blood glucose and lipid concentration by AMPK activation, even when administered in a small dose compared with conventional drugs, as will be confirmed in the following examples. Therefore, the compound of Formula 1 or the pharmaceutically acceptable salt thereof may be effectively used to treat cancer, diabetes mellitus, obesity, hyperlipemia, hypercholesterolemia, fatty liver, coronary artery disease, osteoporosis, polycystic ovary syndrome and metabolic syndrome.

Accordingly, another aspect of the present invention provides a medicine including the compound of Formula 1 or the pharmaceutically acceptable salt thereof as an active ingredient.

Still another aspect of the present invention provides a pharmaceutical composition for preventing or treating a disease selected from the group consisting of cancer, diabetes mellitus, obesity, hyperlipemia, hypercholesterolemia, fatty liver, coronary artery disease, osteoporosis, polycystic ovary syndrome, metabolic syndrome, muscle pain, myocyte damage and rhabdomyolysis, which includes the compound of Formula 1 or the pharmaceutically acceptable salt thereof as an active ingredient, the use of the compound of Formula 1 or the pharmaceutically acceptable salt thereof to prepare medicine for preventing or treating the disease, and a method of preventing or treating the disease including administering a therapeutically effective amount of the compound of Formula 1 or the pharmaceutically acceptable salt thereof to a subject.

According to one exemplary embodiment, the diabetes mellitus may be insulin-independent diabetes mellitus.

The pharmaceutical composition of the present invention includes at least one pharmaceutically acceptable carrier in addition to the active ingredient. As used in this specification, the term "pharmaceutically acceptable carrier" refers to a known pharmaceutically acceptable excipient, which is useful to formulate a pharmaceutically active compound for administration, and is substantially non-toxic and non-sensitive under the conditions it is used. An exact ratio of the excipient is determined by standard pharmaceutical practice, as well as solubility, chemical characteristics and selected route for administration of the active compound.

The pharmaceutical composition of the present invention may be formulated in a form suitable for a desired administration method using a suitable and physiologically acceptable adjuvant such as an excipient, a disintegrating agent, a sweetening agent, a binder, a coating agent, a swelling agent, a lubricating agent, a glossing agent or a flavoring agent.

The pharmaceutical composition may be formulated as a tablet, a capsule, a pill, a granule, powder, an injection or a liquid, but the present invention is not limited thereto.

The formulation and the pharmaceutically available carrier of the pharmaceutical composition may be properly selected according to the techniques known in the art, and for example, may be selected with reference to the following documents: (Urquhart et al., Lancet, 16:367, 1980); (Lieberman et al., Pharmaceutical Dosage Forms-Disperse Systems, 2nd ed., vol. 3, 1998); (Ansel et al., Pharmaceutical Dosage Forms & Drug Delivery Systems, 7th ed., 2000); (Martindale, The Extra Pharmacopeia, 31st ed.); (Remington's Pharmaceutical Sciences, 16th-20th editions); (The Pharmacological Basis of Therapeutics, Goodman and Gilman, eds., 9th ed., 1996); and (Wilson and Gisvolds' Textbook of Organic Medicinal and Pharmaceutical Chemistry, Delgado and Remers, eds., 10th ed., 1998). Also, principles of formulating a pharmaceutical composition may be described, for example, with reference to the following documents: (Platt, Clin Lab Med, 7:289-99, 1987); (Aulton, Pharmaceutics: The Science of Dosage Form Design, Churchill Livingstone, N.Y., 1988); (Extemporaneous Oral Liquid Dosage Preparations, CSHP, 1998); and ("Drug Dosage," J Kans Med Soc, 70(1):30-32, 1969).

According to one exemplary embodiment, the pharmaceutical composition may be used together with a second drug.

According to the present invention, the term "second drug" refers to another pharmaceutically active ingredient in addition to the biguanide derivative according to the present invention. The compound of Formula 1 or the pharmaceutically acceptable salt thereof according to the present invention may be used to treat a variety of diseases, as described above. As a result, the compound of Formula 1 or the pharmaceutically acceptable salt thereof according to the present invention may be used together with a second drug for effectively treating respective diseases. For example, the second drug may be an anti-hyperglycemic agent, an anti-obesity agent, an anticancer agent, etc.

When the compound of Formula 1 or the pharmaceutically acceptable salt thereof according to the present invention and the second drug are able to be administered in the same manner, the compound of Formula 1 or the pharmaceutically acceptable salt thereof may be formulated together with the second drug to be provided in the form of a composite preparation.

Meanwhile, according to the present invention, the term "subject" refers to a warm-blooded animal, such as a mammal, with a specific condition, disorder or disease. For example, a mammal includes a human, an orangutan, a mouse, a rat, a dog, a cow, a chicken, a pig, a goat, a sheep, etc., but the present invention is not limited thereto.

Also, the term "treating" includes relieving a symptom, temporarily or permanently eliminating causes of the symptom, and preventing or hindering occurrence of the symptom or progression of the above-described condition, disorder or disease, but the present invention is not limited thereto.

An effective amount of the active ingredient of the pharmaceutical composition according to the present invention refers to an amount required to treat a disease. Therefore, the effective amount of the active ingredient may be adjusted according to various factors such as kinds and severity of the disease, kinds and contents of the active ingredient and other ingredients included in the composition, kinds of formulation, age, body weight, general medical conditions, sex and diet of a subject, duration and route of administration, a release rate of the composition, treatment duration, and the number of drugs used together. In the case of an adult, for example, the compound of Formula 1 may be administered in a total dose of 50 to 3,000 mg/kg when administered once to several times a day.

Advantageous Effects of Invention

The N1-cyclic amine-N5-substituted phenyl biguanide derivative of Formula 1 according to the present invention is highly effective in inhibiting cancer cell proliferation, cancer metastasis and cancer recurrence, even when administered in a small dose compared with conventional drug, and is also highly effective at lowering blood glucose and lipid concentration. Therefore, the biguanide derivative of Formula 1 according to the present invention may be effectively used to treat diabetes mellitus, obesity, hyperlipemia, hypercholesterolemia, fatty liver, coronary artery disease, osteoporosis, polycystic ovary syndrome and metabolic syndrome, as well as cancer.

MODE FOR THE INVENTION

Figure 1:
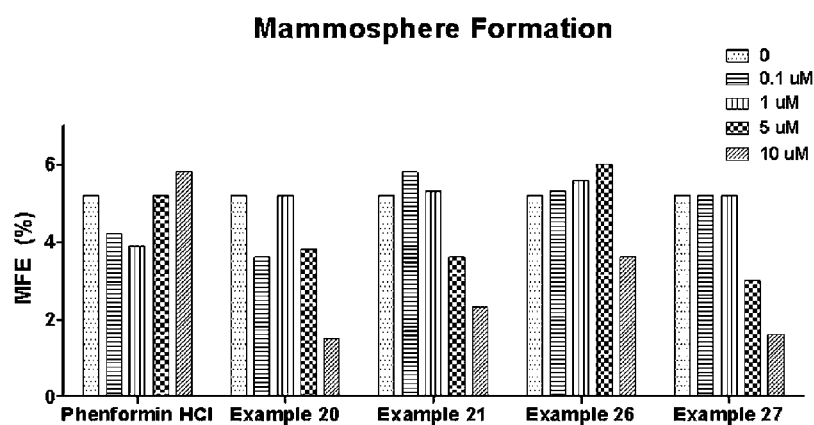
FIG. 1 is a graph showing the mammosphere-forming efficiency (MFE (%)) of a compound represented by Formula 1 according to the present invention.

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example 1

Synthesis of N1-piperidine cyanoguanidine

Concentrated hydrochloric acid (81.7 ml, 0.940 mol) was added to a solution prepared by dissolving piperidine (92.8 ml, 0.940 mol) in butanol (300 ml) and stirred at 0° C. for 30 minutes. Sodium dicyanamide (92.0 g, 1.03 mol) was added to the mixed solution, and the resulting reaction mixture was stirred for 24 hour under reflux. After the completion of the reaction was confirmed, sodium chloride formed by filtering the reaction mixture was removed, and the filtrate was then concentrated at a reduced pressure. Distilled water (100 ml) was added to the concentrate and stirred at room temperature for 1 hour. The formed solid was filtered, and the filter cake was washed with distilled water (2×20 ml). The filter cake was dried at a reduced pressure to obtain a white solid target compound (93.3 g, 65%).

$^1$H NMR (600 MHz, DMSO-$d_6$) δ 7.01 (br, s, 2H), 3.39 (m, 4H), 1.54 (m, 2H), 1.42 (m, 4H); LC-MS m/z 153.2 [M+1]$^+$; mp 163-165° C.

Example 2

Synthesis of N1-azetidine cyanoguanidine

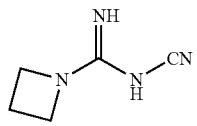

A white solid target compound (1.13 g, 52%) was prepared in the same manner as in Example 1, except that azetidine was used instead of the piperidine which was used in Example 1.

¹H NMR (600 MHz, DMSO-d₆) δ 6.92 (br, s, 2H), 3.91 (t, J=7.8 Hz, 4H), 2.16 (tt, J=7.8, 7.8 Hz, 2H); LC-MS m/z 125.2[M+1]⁺; mp 188-189° C.

Example 3

Synthesis of N1-pyrrolidine cyanoguanidine

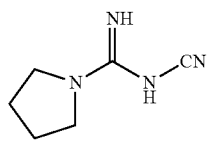

A white solid target compound (24.5 g, 63%) was prepared in the same manner as in Example 1, except that pyrrolidine was used instead of the piperidine which was used in Example 1.

¹H NMR (600 MHz, DMSO-d₆) δ 6.88 (br, s, 2H), 3.24 (m, 4H), 1.80 (m, 4H); LC-MS m/z 139.2[M+1]⁺; mp 232-235° C.

Example 4

Synthesis of N1-azepane cyanoguanidine

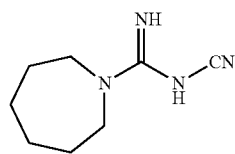 [SMILES: N#CNC(=N)N1CCCCCC1]

A white solid target compound (10.1 g, 60%) was prepared in the same manner as in Example 1, except that azepane was used instead of the piperidine which was used in Example 1.

¹H NMR (600 MHz, DMSO-d₆) δ 6.88 (br, s, 2H), 3.38 (m, 4H), 1.59 (m, 4H), 1.45 (m, 4H); LC-MS m/z 167.2[M+1]⁺; mp 168-170° C.

Example 5

Synthesis of N1-morpholine cyanoguanidine

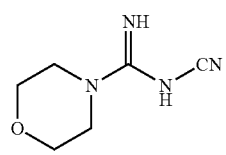 [SMILES: N#CNC(=N)N1CCOCC1]

A white solid target compound (2.04 g, 58%) was prepared in the same manner as in Example 1, except that morpholine was used instead of the piperidine which was used in Example 1.

¹H NMR (600 MHz, DMSO-d₆) δ 7.12 (br, s, 2H), 3.51 (m, 4H), 3.35 (m, 4H); LC-MS m/z 155.1[M+1]⁺; mp 171-173° C.

Example 6

Synthesis of N1-(4-methylpiperazine) cyanoguanidine

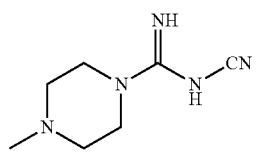

A white solid target compound (1.01 g, 49%) was prepared in the same manner as in Example 1, except that 4-methylpiperazine was used instead of the piperidine which was used in Example 1.

¹H NMR (600 MHz, DMSO-d₆) δ 7.12 (br, s, 2H), 3.39 (t, J=4.8 Hz, 4H), 2.24 (t, J=4.8 Hz, 4H), 2.15 (s, 3H); LC-MS m/z 168.2[M+1]⁺; mp 192-194° C.

Example 7

Preparation of N1-piperidine-N5-(3-bromo)phenyl biguanide hydrochloride

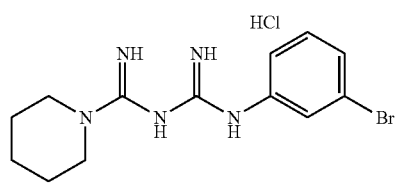 [SMILES: Cl ; N=C(NC(=N)N1CCCCC1)Nc1cccc(Br)c1]

Concentrated hydrochloric acid (0.174 ml, 1.97 mmol) was added to a solution obtained by dissolving (3-bromo)phenylamine (406 mg, 2.36 mmol) in butanol (10 ml) and stirred at room temperature for 30 minutes. The N1-piperidine cyanoguanidine (300 mg, 1.97 mmol) prepared in Example 1 was added to the reaction mixture and stirred for 6 hours under reflux. The reaction mixture was concentrated under reduced pressure, the concentrate was then dissolved while adding a 6N hydrochloric acid/methanol solution (3 ml), and ethyl acetate (1 ml) was added thereto. The formed solid was filtered, and the filter cake was dried under reduced pressure to obtain a white solid target compound (596 mg, 70%).

¹H NMR (600 MHz, DMSO-d₆) δ 9.88 (br, s, 1H), 7.76 (br, s, 1H), 7.72 (s, 1H), 7.30 (ddd, J=7.8, 1.2, 0.6 Hz, 1H), 7.24 (dd, J=7.8, 7.8 Hz, 1H), 7.19 (dd, J=7.8, 0.6 Hz, 1H), 6.93 (br, s, 2H), 3.45 (m, 4H), 1.58 (m, 2H), 1.55 (m, 4H); LC-MS m/z 324.1[M+1]⁺; mp 263-264° C.

Target compounds of the following Examples 8 to 69 were prepared in the same manner as in Example 7, except that the cyanoguanidine and amine compounds synthesized in Examples 2 to 6, which correspond to the target compounds, were used instead of the N1-piperidine cyanoguanidine which was synthesized in Example 1 and the (3-bromo)phenylamine which was used in Example 7.

Example 8

N1-piperidine-N5-phenyl biguanide hydrochloride

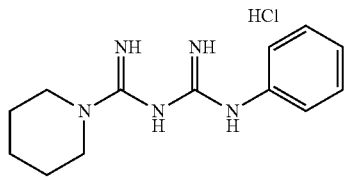 [SMILES: Cl ; N=C(NC(=N)N1CCCCC1)Nc1ccccc1]

$^1$H NMR (600 MHz, DMSO-$d_6$) δ 9.38 (br, s, 1H), 7.69 (br, s, 2H), 7.37 (m, 2H), 7.28 (m, 2H), 7.02 (dd, J=3.9, 3.9 Hz, 1H), 6.92 (br, s, 2H), 3.44 (m, 4H), 1.58 (m, 2H), 1.54 (m, 2H); LC-MS m/z 246.2[M+1]$^+$; mp 204-206° C.

Example 9

N1-piperidine-N5-(3-methyl)phenyl biguanide hydrochloride

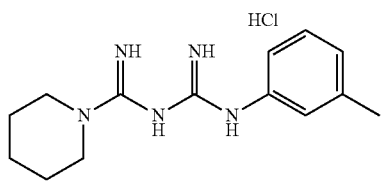 [SMILES: Cl ; Cc1cccc(NC(=N)NC(=N)N2CCCCC2)c1]

$^1$H NMR (600 MHz, DMSO-$d_6$) δ 9.34 (br, s, 1H), 7.56 (br, s, 2H), 7.12 (m, 3H), 6.81 (s, 1H), 6.77 (br, s, 2H), 3.39 (m, 4H), 2.22 (s, 3H), 1.55 (m, 2H), 1.49 (m, 4H); LC-MS m/z 260.2[M+1]$^+$; mp 239-240° C.

Example 10

N1-piperidine-N5-(3-ethyl)phenyl biguanide hydrochloride

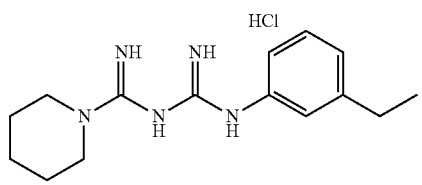 [SMILES: Cl ; CCc1cccc(NC(=N)NC(=N)N2CCCCC2)c1]

$^1$H NMR (400 MHz, DMSO-$d_6$) δ 9.46 (br, s, 1H), 7.61 (br, s, 2H), 7.18 (m, 3H), 6.89 (m, 1H), 6.83 (br, s, 2H), 3.43 (m, 4H), 2.56 (m, 2H), 1.58 (m, 6H), 1.16 (m, 3H); LC-MS m/z 274.2[M+1]$^+$; mp 225-227° C.

Example 11

N1-piperidine-N5-(3-hydroxy)phenyl biguanide hydrochloride

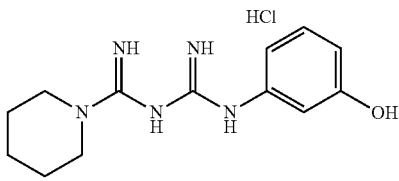 [SMILES: Cl ; N=C(NC(=N)N1CCCCC1)Nc1cccc(O)c1]

$^1$H NMR (600 MHz, DMSO-$d_6$) δ 9.53 (s, 1H), 7.69 (br, s, 2H), 7.04 (t, J=7.8 Hz, 1H), 6.88 (s, 1H), 6.88 (br, s, 2H), 6.76 (d, J=7.8 Hz, 1H), 6.44 (d, J=7.8 Hz, 1H), 3.44 (m, 4H), 1.58 (m, 2H), 1.55 (m, 4H); LC-MS m/z 262.2[M+H]$^+$; mp 210-212° C.

Example 12

N1-piperidine-N5-(3-hydroxymethyl)phenyl biguanide hydrochloride

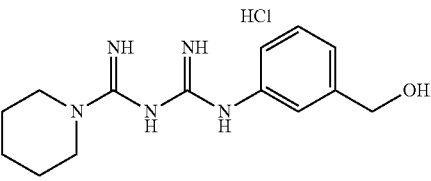 [SMILES: Cl ; N=C(NC(=N)N1CCCCC1)Nc1cccc(CO)c1]

$^1$H NMR (600 MHz, DMSO-$d_6$) δ 9.35 (br, s, 1H), 7.61 (br, s, 2H), 7.29 (s, 1H), 7.23 (m, 2H), 6.98 (d, J=5.4 Hz, 1H), 6.79 (br, s, 2H), 5.20 (t, J=5.2 Hz, 1H), 4.45 (d, J=6.0 Hz, 2H), 3.43 (m, 4H), 1.59 (m, 2H), 1.54 (m, 4H); LC-MS m/z 276.2[M+1]$^+$; mp 225-227° C.

Example 13

N1-piperidine-N5-(3-methoxy)phenyl biguanide hydrochloride

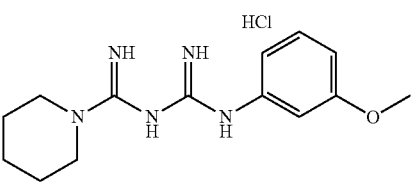 [SMILES: Cl ; COc1cccc(NC(=N)NC(=N)N2CCCCC2)c1]

$^1$H NMR (600 MHz, DMSO-$d_6$) δ 9.42 (br, s, 1H), 7.65 (br, s, 2H), 7.18 (t, J=7.8 Hz, 1H), 7.04 (s, 1H), 6.88 (d, J=7.2 Hz, 1H), 6.81 (br, s, 2H), 6.61 (m, 1H), 3.71 (s, 3H), 3.43 (m, 4H), 1.59 (m, 2H), 1.54 (m, 4H); LC-MS m/z 276.2[M+1]$^+$; mp 230-232° C.

Example 14

N1-piperidine-N5-(4-fluoro)phenyl biguanide hydrochloride

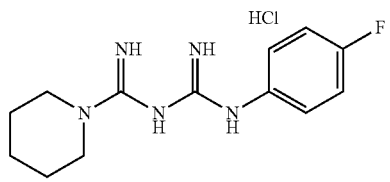 [SMILES: Cl ; N=C(NC(=N)N1CCCCC1)Nc1ccc(F)cc1]

¹H NMR (600 MHz, DMSO-d$_6$) δ 9.58 (br, s, 1H), 7.63 (br, s, 2H), 7.37 (dd, J=9.0, 4.8 Hz, 2H), 7.13 (dd, J=9.0, 9.0 Hz, 2H), 6.83 (br, s, 2H), 3.42 (m, 4H), 1.58 (m, 2H), 1.53 (m, 4H); LC-MS m/z 264.2[M+1]$^+$; mp 269-270° C.

Example 15

N1-piperidine-N5-(2-fluoro)phenyl biguanide hydrochloride

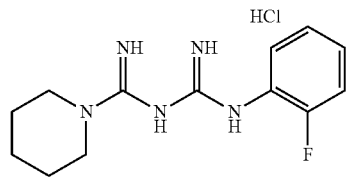 [SMILES: Cl ; N=C(NC(=N)N1CCCCC1)Nc1ccccc1F]

¹H NMR (600 MHz, DMSO-d$_6$) δ 9.61 (br, s, 1H), 7.66 (br, s, 2H), 7.35 (m, 1H), 7.30 (m, 1H), 7.14 (dd, J=8.4, 8.4 Hz, 2H), 6.86 (br, s, 2H), 3.42 (m, 4H), 1.55 (m, 6H); LC-MS m/z 264.2[M+1]$^+$; mp 155-157° C.

Example 16

N1-piperidine-N5-(3-fluoro)phenyl biguanide hydrochloride

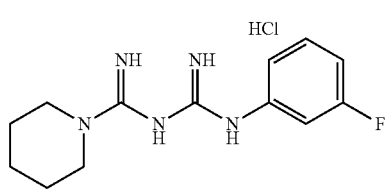 [SMILES: Cl ; N=C(NC(=N)N1CCCCC1)Nc1cccc(F)c1]

¹H NMR (600 MHz, DMSO-d$_6$) δ 9.96 (br, s, 1H), 7.79 (br, s, 2H), 7.37 (s, 1H), 7.28 (s, 1H), 7.20 (s, 1H), 7.11 (d, J=8.4 Hz, 1H), 6.93 (br, s, 2H), 3.46 (m, 4H), 1.56 (m, 6H); LC-MS m/z 264.2[M+1]$^+$; mp 201-202° C.

Example 17

N1-pyrrolidine-N5-(4-chloro)phenyl biguanide hydrochloride

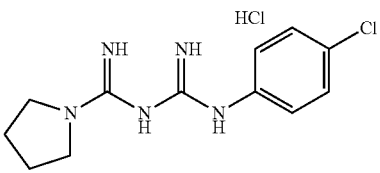 [SMILES: Cl ; N=C(NC(=N)N1CCCC1)Nc1ccc(Cl)cc1]

¹H NMR (600 MHz, DMSO-d$_6$) δ 9.61 (br, s, 1H), 7.58 (br, s, 1H), 7.42 (m, 2H), 7.33 (m, 2H), 6.82 (br, s, 2H), 3.38 (m, 4H), 1.94 (m, 2H), 1.83 (m, 2H); LC-MS m/z 266.2 [M+1]$^+$; mp 260-261° C.

Example 18

N1-piperidine-N5-(4-chloro)phenyl biguanide hydrochloride

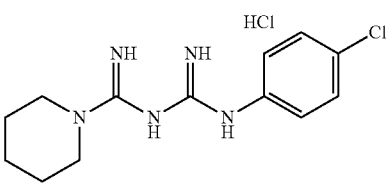 [SMILES: Cl ; N=C(NC(=N)N1CCCCC1)Nc1ccc(Cl)cc1]

¹H NMR (600 MHz, DMSO-d$_6$) δ 9.96 (br, s, 1H), 7.70 (br, s, 1H), 7.39 (d, J=8.7 Hz, 2H), 7.22 (dd, J=8.7, 1.8 Hz, 2H), 6.85 (br, s, 2H), 3.43 (m, 4H), 1.58 (m, 2H), 1.54 (m, 4H); LC-MS m/z 280.2[M+1]$^+$; mp 275-276° C.

Example 19

N1-pyrrolidine-N5-(3-chloro)phenyl biguanide hydrochloride

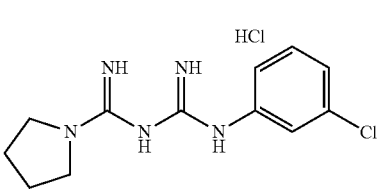 [SMILES: Cl ; N=C(NC(=N)N1CCCC1)Nc1cccc(Cl)c1]

¹H NMR (600 MHz, DMSO-d$_6$) δ 10.04 (br, s, 1H), 7.63 (br, s, 2H), 7.58 (s, 1H), 7.26 (m, 2H), 7.00 (d, J=6.0 Hz, 1H), 6.91 (br, s, 2H), 3.26 (m, 4H), 1.80 (m, 4H); LC-MS m/z 266.2[M+1]$^+$; mp 170-172° C.

Example 20

N1-piperidine-N5-(3-chloro)phenyl biguanide hydrochloride

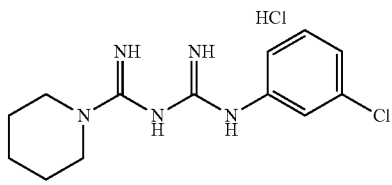 [SMILES: Cl ; N=C(NC(=N)N1CCCCC1)Nc1cccc(Cl)c1]

$^1$H NMR (600 MHz, DMSO-d$_6$) δ 10.10 (br, s, 1H), 7.81 (br, s, 2H), 7.60 (s, 1H), 7.49 (s, 1H), 7.28 (m, 1H), 7.05 (d, J=7.2 Hz, 1H), 6.98 (br, s, 2H), 3.38 (m, 4H), 1.55 (m, 4H); LC-MS m/z 280.2[M+1]$^+$; mp 172-174° C.

Example 21

N1-azepane-N5-(3-chloro)phenyl biguanide hydrochloride

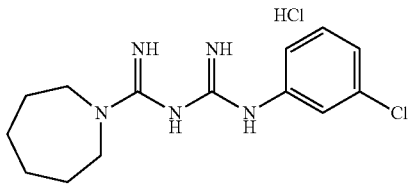 [SMILES: Cl ; N=C(NC(=N)N1CCCCCC1)Nc1cccc(Cl)c1]

$^1$H NMR (600 MHz, DMSO-d$_6$) δ 8.82 (br, s, 1H), 7.71 (d, J=7.8 Hz, 1H), 7.62 (br, s, 1H), 7.46 (d, J=7.8 Hz, 1H), 7.29 (dd, J=7.8, 7.8 Hz, 1H), 7.16 (br, s, 2H), 7.12 (dd, J=7.8, 7.8 Hz, 1H), 3.41 (m, 4H), 1.68 (m, 2H), 1.49 (m, 6H); LC-MS m/z 294.2[M+1]$^+$; mp 213-215° C.

Example 22

N1-morpholine-N5-(3-bromo)phenyl biguanide hydrochloride

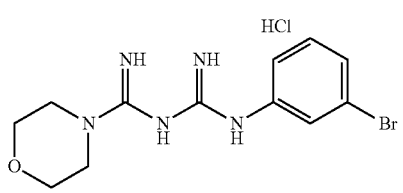 [SMILES: Cl ; N=C(NC(=N)N1CCOCC1)Nc1cccc(Br)c1]

$^1$H NMR (600 MHz, DMSO-d$_6$) δ 9.80 (br, s, 1H), 7.86 (br, s, 1H), 7.65 (br, s, 1H), 7.30 (d, J=7.8 Hz, 1H), 7.25 (dd, J=7.8, 7.8 Hz, 1H), 7.21 (dd, J=7.8, 1.2 Hz, 1H), 7.01 (br, s, 2H), 3.64 (t, J=4.8 Hz, 2H), 3.46 (t, J=4.8 Hz, 2H); LC-MS m/z 326.3[M+1]$^+$; mp 264-265° C.

Example 23

N1-pyrrolidine-N5-(3-trifluoromethyl)phenyl biguanide hydrochloride

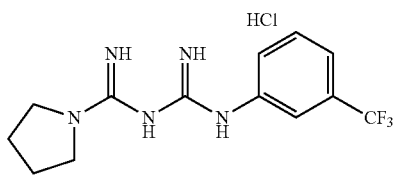 [SMILES: Cl ; N=C(NC(=N)N1CCCC1)Nc1cccc(C(F)(F)F)c1]

$^1$H NMR (600 MHz, DMSO-d$_6$) δ 9.93 (br, s, 1H), 7.86 (s, 1H), 7.68 (br, s, 2H), 7.65 (d, J=8.4 Hz, 1H), 7.51 (dd, J=8.4, 7.2 Hz, 1H), 7.34 (d, J=7.2 Hz, 1H), 6.92 (br, s, 2H), 3.35 (m, 4H), 1.94 (m, 2H), 1.84 (m, 2H); LC-MS m/z 300.1[M+1]$^+$; mp 286-287° C.

Example 24

N1-piperidine-N5-(3-trifluoromethyl)phenyl biguanide hydrochloride

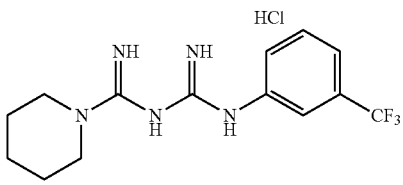 [SMILES: Cl ; N=C(NC(=N)N1CCCCC1)Nc1cccc(C(F)(F)F)c1]

$^1$H NMR (600 MHz, DMSO-d$_6$) δ 9.94 (br, s, 1H), 7.77 (br, s, 2H), 7.59 (d, J=7.8 Hz, 1H), 7.51 (dd, J=7.8, 7.8 Hz, 1H), 7.35 (d, J=7.8 Hz, 1H), 6.94 (br, s, 2H), 3.45 (m, 4H), 1.59 (m, 2H), 1.54 (m, 4H); LC-MS m/z 314.3[M+1]$^+$; mp 264-265° C.

Example 25

N1-azetidine-N5-(4-trifluoromethyl)phenyl biguanide hydrochloride

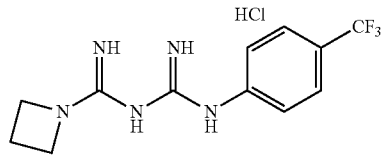 [SMILES: Cl ; N=C(NC(=N)N1CCC1)Nc1ccc(C(F)(F)F)cc1]

$^1$H NMR (600 MHz, DMSO-d$_6$) δ 9.91 (br, s, 1H), 7.64 (br, s, 2H), 7.63 (d, J=9.0 Hz, 2H), 7.59 (d, J=9.0 Hz, 2H), 7.06 (br, s, 2H), 4.04 (m, 4H), 2.26 (m, 2H); LC-MS m/z 286.2[M+1]$^+$; mp 258-259° C.

Example 26

N1-pyrrolidine-N5-(4-trifluoromethyl)phenyl biguanide hydrochloride

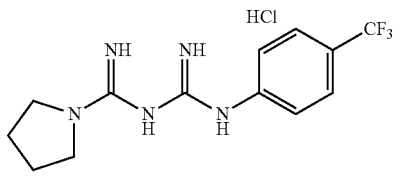 [SMILES: Cl ; N=C(NC(=N)N1CCCC1)Nc1ccc(C(F)(F)F)cc1]

$^1$H NMR (600 MHz, DMSO-d$_6$) δ 10.07 (br, s, 1H), 7.71 (br, s, 2H), 7.63 (m, 4H), 6.97 (br, s, 2H), 3.35 (m, 4H), 1.95 (m, 2H), 1.84 (m, 2H); LC-MS m/z 300.1[M+1]$^+$; mp 283-284° C.

Example 27

N1-piperidine-N5-(4-trifluoromethyl)phenyl biguanide hydrochloride

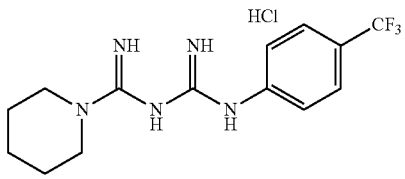 [SMILES: Cl ; N=C(NC(=N)N1CCCCC1)Nc1ccc(C(F)(F)F)cc1]

$^1$H NMR (600 MHz, DMSO-d$_6$) δ 10.03 (br, s, 1H), 7.84 (br, s, 2H), 7.64 (d, J=9.0 Hz, 2H), 7.59 (d, J=9.0 Hz, 2H), 6.96 (br, s, 2H), 3.44 (m, 4H), 1.58 (m, 2H), 1.56 (m, 4H); LC-MS m/z 314.3[M+1]$^+$; mp 273-274° C.

Example 28

N1-pyrrolidine-N5-(3-trifluoromethoxy)phenyl biguanide hydrochloride

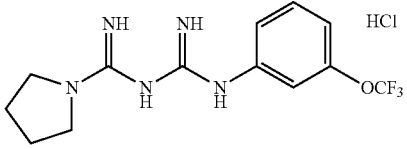 [SMILES: N=C(NC(=N)N1CCCC1)Nc1cccc(OC(F)(F)F)c1 ; Cl]

$^1$H NMR (600 MHz, DMSO-d$_6$) δ 9.78 (br, s, 1H), 7.64 (br, s, 2H), 7.55 (s, 1H), 7.39 (dd, J=8.4, 8.4 Hz, 1H), 7.35 (d, J=8.4 Hz, 1H), 6.97 (d, J=8.4 Hz, 1H), 6.85 (br, s, 2H), 3.35 (m, 4H), 1.95 (m, 2H), 1.84 (m, 2H); LC-MS m/z 316.2[M+1]$^+$; mp 261-262° C.

Example 29

N1-piperidine-N5-(3-trifluoromethoxy)phenyl biguanide hydrochloride

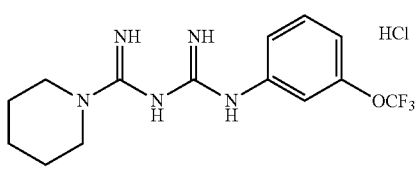 [SMILES: N=C(NC(=N)N1CCCCC1)Nc1cccc(OC(F)(F)F)c1 ; Cl]

$^1$H NMR (600 MHz, DMSO-d$_6$) δ 9.57 (br, s, 1H), 7.76 (br, s, 2H), 7.53 (s, 1H), 7.40 (t, J=8.4 Hz, 1H), 7.29 (d, J=7.2 Hz, 1H), 6.99 (d, J=7.8 Hz, 1H), 6.82 (br, s, 2H), 3.43 (m, 4H), 1.60 (m, 2H), 1.54 (m, 4H); LC-MS m/z 330.2 [M+1]$^+$; mp 264-266° C.

Example 30

N1-piperidine-N5-(3-difluoromethoxy)phenyl biguanide hydrochloride

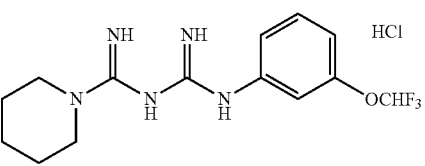

$^1$H NMR (600 MHz, DMSO-d$_6$) δ 9.43 (br, s, 1H), 7.71 (br, s, 2H), 7.33 (d, J=8.4 Hz, 2H), 7.15 (s, 1H), 6.82 (m, 2H), 6.80 (br, s, 2H), 3.44 (m, 4H), 1.59 (m, 2H), 1.54 (m, 4H); LC-MS m/z 312.3[M+1]$^+$; mp 244-245° C.

Example 31

N1-azetidine-N5-(4-trifluoromethoxy)phenyl biguanide hydrochloride

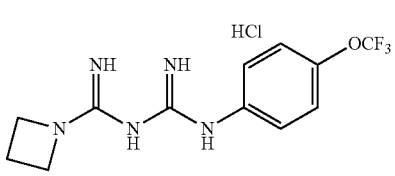 [SMILES: Cl ; N=C(NC(=N)N1CCC1)Nc1ccc(OC(F)(F)F)cc1]

$^1$H NMR (600 MHz, DMSO-d$_6$) δ 9.91 (br, s, 1H), 7.53 (br, s, 2H), 7.47 (d, J=9.0 Hz, 2H), 7.30 (d, J=9.0 Hz, 2H), 6.94 (br, s, 2H), 4.02 (m, 4H), 2.26 (m, 2H); LC-MS m/z 302.1[M+1]$^+$; mp 257-259° C.

Example 32

N1-pyrrolidine-N5-(4-trifluoromethoxy)phenyl biguanide hydrochloride

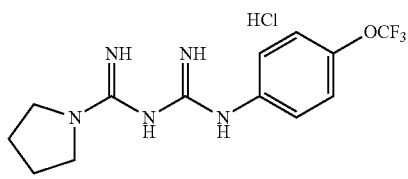 [SMILES: Cl ; N=C(NC(=N)N1CCCC1)Nc1ccc(OC(F)(F)F)cc1]

$^1$H NMR (600 MHz, DMSO-d$_6$) δ 9.60 (d, J=5.4 Hz, 1H), 7.58 (br, s, 2H), 7.51 (d, J=9.0 Hz, 2H), 7.28 (d, J=9.0 Hz, 2H), 6.81 (br, s, 2H), 3.34 (m, 4H), 1.94 (m, 2H), 1.84 (m, 2H); LC-MS m/z 316.2[M+1]$^+$; mp 281-282° C.

Example 33

N1-piperidine-N5-(4-trifluoromethoxy)phenyl biguanide hydrochloride

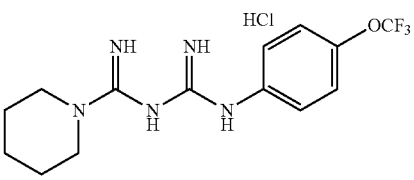 [SMILES: Cl ; N=C(NC(=N)N1CCCCC1)Nc1ccc(OC(F)(F)F)cc1]

$^1$H NMR (600 MHz, DMSO-d$_6$) δ 9.55 (br, s, 1H), 7.71 (br, s, 2H), 7.47 (d, J=8.4 Hz, 2H), 7.30 (d, J=9.0 Hz, 2H), 6.82 (br, s, 2H), 3.42 (m, 4H), 1.59 (m, 2H), 1.55 (m, 4H); LC-MS m/z 330.2[M+H]$^+$; mp 277.3° C.

Example 34

N1-morpholine-N5-(4-trifluoromethoxy)phenyl biguanide hydrochloride

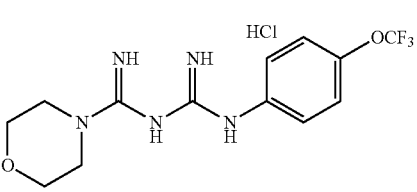 [SMILES: Cl ; N=C(NC(=N)N1CCOCC1)Nc1ccc(OC(F)(F)F)cc1]

$^1$H NMR (600 MHz, DMSO-d$_6$) δ 9.64 (br, s, 1H), 7.83 (br, s, 2H), 7.45 (d, J=8.4 Hz, 2H), 7.31 (d, J=8.4 Hz, 2H), 6.97 (br, s, 2H), 3.63 (t, J=4.8 Hz, 2H), 3.44 (t, J=4.8 Hz, 2H); LC-MS m/z 332.2[M+1]$^+$; mp 263-264° C.

Example 35

N1-(4-methyl)piperazine-N5-(4-trifluoromethoxy)phenyl biguanide hydrochloride

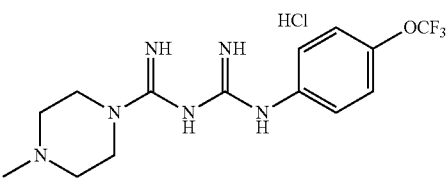 [SMILES: Cl ; CN1CCN(C(=N)NC(=N)Nc2ccc(OC(F)(F)F)cc2)CC1]

$^1$H NMR (600 MHz, DMSO-d$_6$) δ 10.10 (br, s, 1H), 7.84 (br, s, 2H), 7.47 (d, J=8.8 Hz, 2H), 7.29 (d, J=8.8 Hz, 2H), 7.04 (br, s, 2H), 3.46 (m, 4H), 2.35 (m, 4H), 2.19 (s, 3H); LC-MS m/z 345.1[M+1]$^+$; mp 258-259° C.

Example 36

N1-piperidine-N5-(3-amino)phenyl biguanide hydrochloride

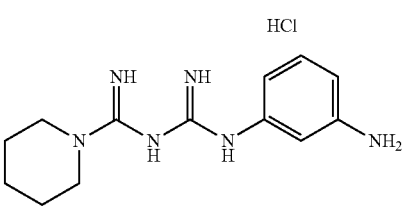 [SMILES: Cl ; N=C(NC(=N)N1CCCCC1)Nc1cccc(N)c1]

$^1$H NMR (600 MHz, DMSO-d$_6$) δ 9.12 (br, s, 1H), 7.53 (br, s, 2H), 6.90 (t, J=7.8 Hz, 1H), 6.73 (br, s, 2H), 6.55 (s, 1H), 6.51 (d, J=6.0 Hz, 1H), 6.25 (d, J=6.0 Hz, 1H), 5.06 (br, s, 2H), 3.42 (m, 4H), 1.59 (m, 2H), 1.54 (m, 4H); LC-MS m/z 261.2[M+1]$^+$; mp 220-222° C.

Example 37

N1-piperidine-N5-(4-dimethylamino)phenyl biguanide hydrochloride

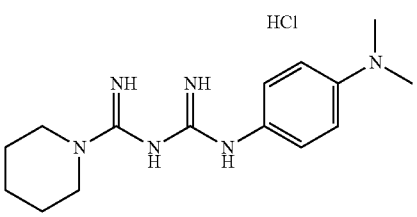 [SMILES: CN(C)c1ccc(NC(=N)NC(=N)N2CCCCC2)cc1 ; Cl]

$^1$H NMR (600 MHz, DMSO-d$_6$) δ 8.95 (br, s, 1H), 7.40 (br, s, 2H), 7.12 (d, J=9.0 Hz, 2H), 6.68 (m, 4H), 3.39 (m, 4H), 2.85 (s, 6H), 1.57 (m, 2H), 1.51 (m, 4H); LC-MS m/z 289.1[M+H]$^+$; mp 253-255° C.

Example 38

N1-piperidine-N5-(4-acetamide)phenyl biguanide hydrochloride

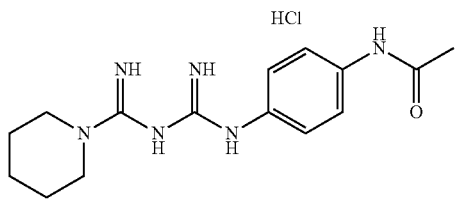 [SMILES: Cl ; CC(=O)Nc1ccc(NC(=N)NC(=N)N2CCCCC2)cc1]

$^1$H NMR (600 MHz, DMSO-d$_6$) δ 9.96 (br, s, 1H), 9.34 (br, s, 1H), 7.57 (br, s, 2H), 7.49 (d, J=9.6 Hz, 2H), 7.24 (d, J=9.6 Hz, 2H), 6.79 (br, s, 2H), 3.41 (m, 4H), 1.58 (m, 2H), 1.52 (m, 4H); LC-MS m/z 303.2[M+1]$^+$; mp 258-260° C.

Example 39

N1-piperidine-N5-(3-acetamide)phenyl biguanide hydrochloride

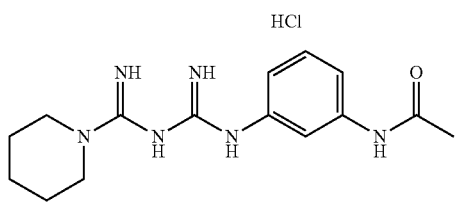 [SMILES: Cl ; CC(=O)Nc1cccc(NC(=N)NC(=N)N2CCCCC2)c1]

$^1$H NMR (600 MHz, DMSO-d$_6$) δ 10.01 (br, s, 1H), 9.47 (br, s, 1H), 7.67 (br, s, 2H), 7.65 (s, 1H), 7.16 (m, 2H), 7.09 (m, 1H), 6.80 (br, s, 2H), 3.43 (m, 4H), 2.02 (s, 3H), 1.55 (m, 6H); LC-MS m/z 303.2[M+1]$^+$; mp 265-267° C.

Example 40

N1-piperidine-N5-(4-(1H-tetrazole-5-yl))phenyl biguanide hydrochloride

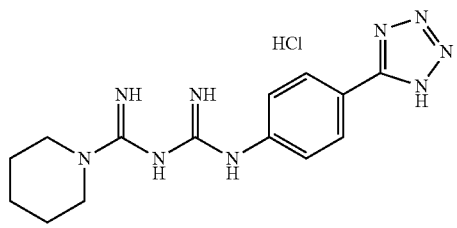 [SMILES: N=C(NC(=N)N1CCCCC1)Nc1ccc(-c2nnn[nH]2)cc1 ; Cl]

$^1$H NMR (600 MHz, DMSO-d$_6$) δ 9.91 (br, s, 1H), 7.99 (d, J=9.0 Hz, 2H), 7.80 (br, s, 2H), 7.58 (d, J=9.0 Hz, 2H), 6.95 (br, s, 2H), 3.46 (m, 4H), 1.58 (m, 6H); LC-MS m/z 314.2[M+1]$^+$; mp 241-242° C.

Example 41

N1-piperidine-N5-(3-methylsulfonamide)phenyl biguanide hydrochloride

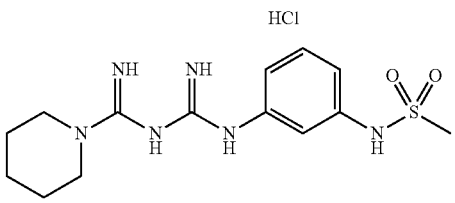 [SMILES: Cl ; CS(=O)(=O)Nc1cccc(NC(=N)NC(=N)N2CCCCC2)c1]

$^1$H NMR (600 MHz, DMSO-d$_6$) δ 9.22 (br, s, 1H), 7.63 (br, s, 2H), 7.28 (s, 1H), 7.22 (t, J=8.4 Hz, 1H), 7.09 (d, J=7.8 Hz, 1H), 6.85 (m, 1H), 6.70 (br, s, 2H), 3.45 (m, 4H), 2.97 (s, 3H), 1.59 (m, 2H), 1.55 (m, 4H); LC-MS m/z 339.2[M+1]$^+$; mp 251-253° C.

Example 42

N1-piperidine-N5-(4-sulfonic acid)phenyl biguanide hydrochloride

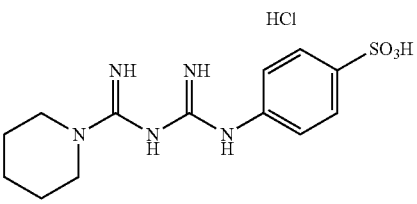 [SMILES: Cl ; N=C(NC(=N)N1CCCCC1)Nc1ccc(S(=O)(=O)O)cc1]

$^1$H NMR (600 MHz, DMSO-d$_6$) δ 9.10 (br, s, 1H), 7.58 (br, s, 2H), 7.47 (d, J=4.8 Hz, 2H), 7.23 (d, J=5.4 Hz, 2H), 6.66 (br, s, 2H), 3.38 (m, 4H), 1.55 (m, 2H), 1.50 (m, 4H); LC-MS m/z 341.1[M+H]$^+$; mp 305-307° C.

Example 43

N1-piperidine-N5-(4-methylthio)phenyl biguanide hydrochloride

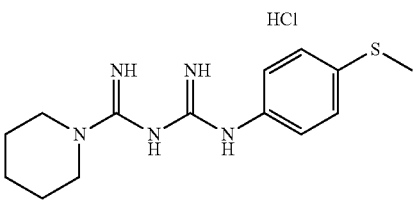 [SMILES: Cl ; CSc1ccc(NC(=N)NC(=N)N2CCCCC2)cc1]

$^1$H NMR (600 MHz, DMSO-d$_6$) δ 0.34 (br, s, 1H), 7.58 (br, s, 2H), 7.26 (d, J=7.8 Hz, 2H), 7.18 (d, J=4.8 Hz, 2H), 6.74 (br, s, 2H), 3.38 (m, 4H), 2.39 (s, 3H), 1.55 (m, 2H), 1.50 (m, 4H); LC-MS m/z 292.3[M+H]$^+$; mp 264-265° C.

Example 44

N1-piperidine-N5-(4-sulfamoyl)phenyl biguanide hydrochloride

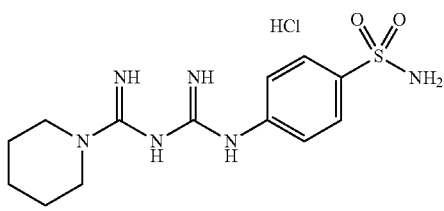 [SMILES: N=C(NC(=N)N1CCCCC1)Nc1ccc(S(N)(=O)=O)cc1 ; Cl]

$^{1}$H NMR (600 MHz, DMSO-$d_{6}$) δ 10.22 (br, s, 1H), 7.84 (br, s, 2H), 7.71 (d, J=8.4 Hz, 2H), 7.56 (d, J=8.4 Hz, 2H), 7.22 (br, s, 2H), 7.01 (br, s, 2H), 3.45 (m, 4H), 1.58 (m, 6H); LC-MS m/z 325.2[M+H]$^{+}$; mp 263-365° C.

Example 45

N1-piperidine-N5-(3,5-dimethoxy)phenyl biguanide hydrochloride

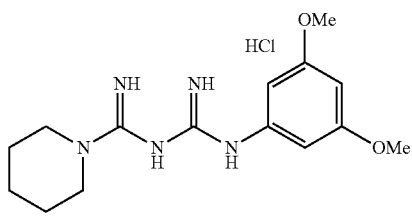 [SMILES: COc1cc(NC(=N)NC(=N)N2CCCCC2)cc(OC)c1 ; Cl]

$^{1}$H NMR (600 MHz, DMSO-$d_{6}$) δ 9.55 (br, s, 1H), 7.70 (br, s, 2H), 6.88 (br, s, 2H), 6.59 (s, 2H), 6.20 (s, 1H), 3.70 (s, 6H), 3.45 (m, 4H), 1.59 (m, 2H), 1.55 (m, 4H); LC-MS m/z 306.3[M+1]$^{+}$; mp 234-236° C.

Example 46

N1-piperidine-N5-(4-fluoro-3-trifluoromethyl)phenyl biguanide hydrochloride

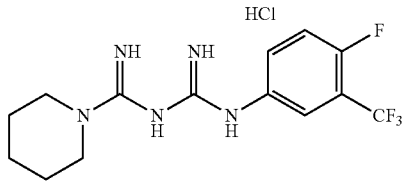 [SMILES: Cl ; N=C(NC(=N)N1CCCCC1)Nc1ccc(F)c(C(F)(F)F)c1]

$^{1}$H NMR (600 MHz, DMSO-$d_{6}$) δ 10.37 (br, s, 1H), 7.88 (m, 1H), 7.83 (br, s, 2H), 7.65 (m, 1H), 7.45 (dd, J=9.6, 9.6 Hz, 1H), 7.03 (br, s, 2H), 3.45 (m, 4H), 1.58 (m, 2H), 1.53 (m, 4H); LC-MS m/z 332.2[M+1]$^{+}$; mp 269-270° C.

Example 47

N1-piperidine-N5-(4-chloro-3-trifluoromethyl)phenyl biguanide hydrochloride

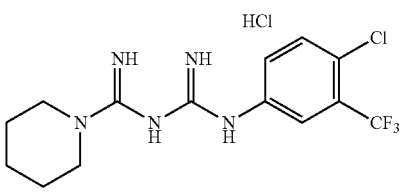 [SMILES: Cl ; N=C(NC(=N)N1CCCCC1)Nc1ccc(Cl)c(C(F)(F)F)c1]

$^{1}$H NMR (600 MHz, DMSO-$d_{6}$) δ 9.87 (br, s, 1H), 7.97 (s, 1H), 7.82 (br, s, 2H), 7.64 (d, J=9.0 Hz, 1H), 7.61 (d, J=9.0 Hz, 1H), 6.94 (br, s, 2H), 3.44 (m, 4H), 1.59 (m, 2H), 1.54 (m, 4H); LC-MS m/z 348.1[M+1]$^{+}$; mp 269-270° C.

Example 48

N1-pyrrolidine-N5-(3-fluoro-4-trifluoromethyl)phenyl biguanide hydrochloride

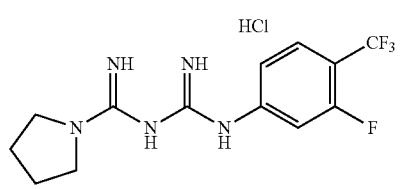 [SMILES: Cl ; N=C(NC(=N)N1CCCC1)Nc1ccc(C(F)(F)F)c(F)c1]

$^{1}$H NMR (400 MHz, DMSO-$d_{6}$) δ 10.42 (br, s, 1H), 7.80 (br, s, 2H), 7.73 (d, J=14.0 Hz, 1H), 7.66 (dd, J=9.0, 8.4 Hz, 1H), 7.30 (d, J=8.4 Hz, 1H), 7.03 (br, s, 2H), 3.36 (m, 4H), 1.95 (m, 2H), 1.84 (m, 2H); LC-MS m/z 318.2[M+1]$^{+}$; mp 253-254° C.

Example 49

N1-piperidine-N5-(3-fluoro-4-trifluoromethyl)phenyl biguanide hydrochloride

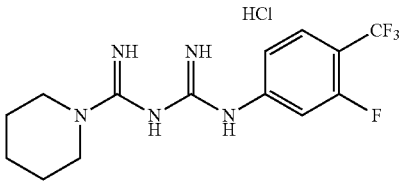 [SMILES: Cl ; N=C(NC(=N)N1CCCCC1)Nc1ccc(C(F)(F)F)c(F)c1]

$^{1}$H NMR (600 MHz, DMSO-$d_{6}$) δ 10.35 (br, s, 1H), 7.94 (br, s, 2H), 7.68 (s, 1H), 7.66 (d, J=8.4 Hz, 1H), 7.28 (d, J=8.4 Hz, 1H), 7.03 (br, s, 2H), 3.45 (m, 4H), 1.51 (m, 6H); LC-MS m/z 332.2[M+1]$^{+}$; mp 263-264° C.

Example 50

N1-piperidine-N5-(4-fluoro-3-trifluoromethoxy) phenyl biguanide hydrochloride

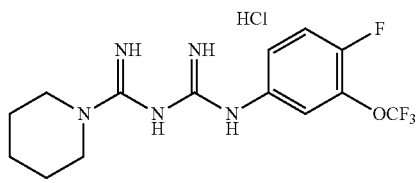 [SMILES: Cl ; N=C(NC(=N)N1CCCCC1)Nc1ccc(F)c(OC(F)(F)F)c1]

¹H NMR (600 MHz, DMSO-d₆) δ 9.95 (br, s, 1H), 7.78 (br, s, 2H), 7.70 (m, 1H), 7.44 (dd, J=9.6, 9.6 Hz, 1H), 7.34 (m, 1H), 6.93 (br, s, 2H), 3.44 (m, 4H), 1.59 (m, 2H), 1.53 (m, 4H); LC-MS m/z 348.2[M+1]⁺; mp 260-261° C.

Example 51

N1-piperidine-N5-(4-chloro-3-trifluoromethoxy) phenyl biguanide hydrochloride

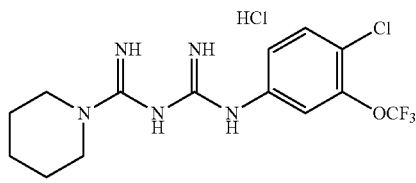 [SMILES: Cl ; N=C(NC(=N)N1CCCCC1)Nc1ccc(Cl)c(OC(F)(F)F)c1]

¹H NMR (600 MHz, DMSO-d₆) δ 10.21 (br, s, 1H), 7.85 (br, s, 2H), 7.79 (s, 1H), 7.58 (d, J=8.4 Hz, 1H), 7.35 (dd, J=8.4, 2.4 Hz, 1H), 6.99 (br, s, 2H), 3.45 (m, 4H), 1.60 (m, 2H), 1.54 (m, 4H); LC-MS m/z 364.1[M+1]⁺; mp 251-252° C.

Example 52

N1-azetidine-N5-(3-fluoro-4-trifluoromethoxy)phenyl biguanide hydrochloride

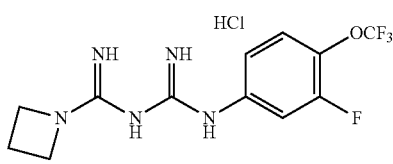 [SMILES: Cl ; N=C(NC(=N)N1CCC1)Nc1ccc(OC(F)(F)F)c(F)c1]

¹H NMR (600 MHz, DMSO-d₆) δ 9.87 (br, s, 1H), 7.66 (m, 3H), 7.47 (dd, J=8.4, 8.4 Hz, 1H), 7.16 (d, J=8.4 Hz, 1H), 7.01 (br, s, 2H), 4.03 (m, 4H), 2.26 (m, 2H); LC-MS m/z 320.2[M+1]⁺; mp 260-261° C.

Example 53

N1-pyrrolidine-N5-(3-fluoro-4-trifluoromethoxy) phenyl biguanide hydrochloride

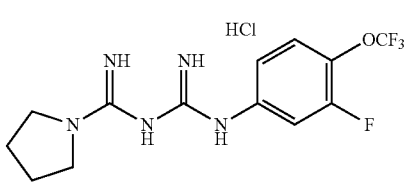 [SMILES: Cl ; N=C(NC(=N)N1CCCC1)Nc1ccc(OC(F)(F)F)c(F)c1]

¹H NMR (400 MHz, DMSO-d₆) δ 9.82 (br, s, 1H), 7.68 (m, 3H), 7.47 (dd, J=9.2, 8.8 Hz, 1H), 7.20 (d, J=9.2 Hz, 1H), 6.87 (br, s, 2H), 3.35 (m, 4H), 1.93 (m, 2H), 1.83 (m, 2H); LC-MS m/z 334.1[M+1]⁺; mp 278-279° C.

Example 54

N1-piperidine-N5-(3-fluoro-4-trifluoromethoxy) phenyl biguanide hydrochloride

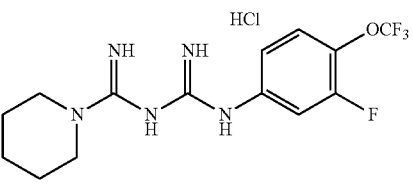 [SMILES: Cl ; N=C(NC(=N)N1CCCCC1)Nc1ccc(OC(F)(F)F)c(F)c1]

¹H NMR (600 MHz, DMSO-d₆) δ 10.09 (br, s, 1H), 7.85 (br, s, 2H), 7.64 (d, J=9.0 Hz, 1H), 7.48 (dd, J=9.0, 9.0 Hz, 1H), 7.19 (dd, J=9.0, 1.2 Hz, 1H), 6.95 (br, s, 2H), 3.44 (m, 4H), 1.57 (m, 6H); LC-MS m/z 348.3[M+1]⁺; mp 262-263° C.

Example 55

N1-azetidine-N5-(3-chloro-4-trifluoromethoxy)phenyl biguanide hydrochloride

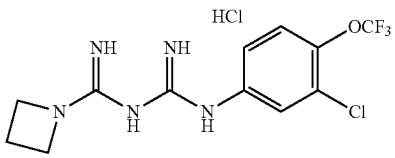 [SMILES: Cl ; N=C(NC(=N)N1CCC1)Nc1ccc(OC(F)(F)F)c(Cl)c1]

¹H NMR (400 MHz, DMSO-d₆) δ 9.91 (br, s, 1H), 7.79 (dd, J=1.6, 0.8 Hz, 1H), 7.66 (br, s, 2H), 7.49 (d, J=9.2 Hz, 1H), 7.37 (ddd, J=9.2, 1.6, 0.8 Hz, 1H), 7.05 (br, s, 2H), 4.04 (m, 4H), 2.26 (m, 2H); LC-MS m/z 336.1[M+1]⁺; mp 254-255° C.

Example 56

N1-pyrrolidine-N5-(3-chloro-4-trifluoromethoxy) phenyl biguanide hydrochloride

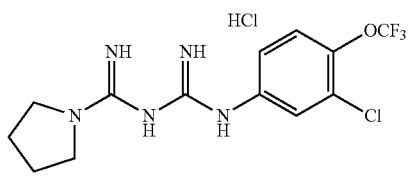 [SMILES: Cl ; N=C(NC(=N)N1CCCC1)Nc1ccc(OC(F)(F)F)c(Cl)c1]

¹H NMR (400 MHz, DMSO-d₆) δ 10.23 (br, s, 1H), 7.82 (d, J=2.4 Hz, 1H), 7.71 (br, s, 2H), 7.48 (d, J=9.0 Hz, 1H), 7.37 (dd, J=9.0, 2.4 Hz, 1H), 6.93 (br, s, 2H), 3.36 (m, 4H), 1.94 (m, 2H), 1.85 (m, 2H); LC-MS m/z 250.1[M+1]⁺; mp 275-276° C.

Example 57

N1-piperidine-N5-(3-chloro-4-trifluoromethoxy) phenyl biguanide hydrochloride

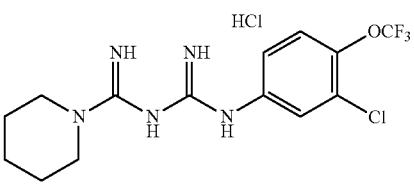 [SMILES: Cl ; N=C(NC(=N)N1CCCCC1)Nc1ccc(OC(F)(F)F)c(Cl)c1]

¹H NMR (600 MHz, DMSO-d₆) δ 9.91 (br, s, 1H), 7.83 (br, s, 2H), 7.78 (d, J=3.0 Hz, 1H), 7.49 (d, J=9.0 Hz, 1H), 7.37 (dd, J=9.0, 3.0 Hz, 1H), 6.94 (br, s, 2H), 3.44 (m, 4H), 1.59 (m, 2H), 1.56 (m, 4H); LC-MS m/z 364.1[M+1]⁺; mp 261-262° C.

Example 58

N1-piperidine-N5-(2,4-difluoro)phenyl biguanide hydrochloride

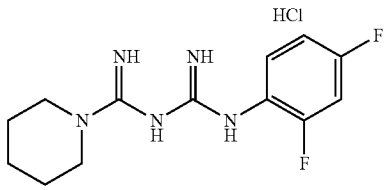 [SMILES: Cl ; N=C(NC(=N)N1CCCCC1)Nc1ccc(F)cc1F]

¹H NMR (600 MHz, DMSO-d₆) δ 9.00 (br, s, 1H), 7.67-7.63 (m, 3H), 7.30 (m, 1H), 7.06 (m, 1H), 7.01 (br, s, 2H), 3.40 (m, 4H), 1.57 (m, 2H), 1.51 (m, 4H); LC-MS m/z 282.3[M+1]⁺; mp 256-257° C.

Example 59

N1-piperidine-N5-(3,4-difluoro)phenyl biguanide hydrochloride

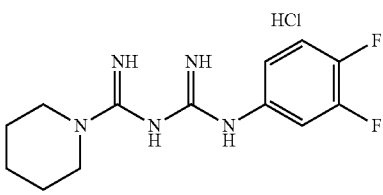 [SMILES: Cl ; N=C(NC(=N)N1CCCCC1)Nc1ccc(F)c(F)c1]

¹H NMR (600 MHz, DMSO-d₆) δ 9.67 (br, s, 1H), 7.73 (br, s, 2H), 7.54 (ddd, J=13.2, 7.2, 3.0 Hz, 1H), 7.36 (dd, J=13.2, 9.0 Hz, 1H), 7.10 (m, 1H), 6.85 (br, s, 2H), 3.43 (m, 4H), 1.58 (m, 2H), 1.54 (m, 4H); LC-MS m/z 282.3[M+1]⁺; mp 257-258° C.

Example 60

N1-piperidine-N5-(3,5-difluoro)phenyl biguanide hydrochloride

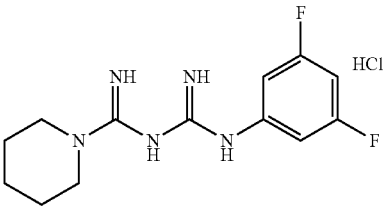 [SMILES: N=C(NC(=N)N1CCCCC1)Nc1cc(F)cc(F)c1 ; Cl]

¹H NMR (600 MHz, DMSO-d₆) δ 10.31 (br, s, 1H), 7.88 (br, s, 2H), 7.14 (dd, J=9.6, 2.0 Hz, 2H), 6.98 (br, s, 2H), 6.82 (ddd, J=9.6, 9.6, 2.0 Hz, 1H), 3.45 (m, 4H), 1.58 (m, 6H); LC-MS m/z 282.3[M+1]⁺; mp 243-244° C.

Example 61

N1-piperidine-N5-(3,5-dichloro)phenyl biguanide hydrochloride

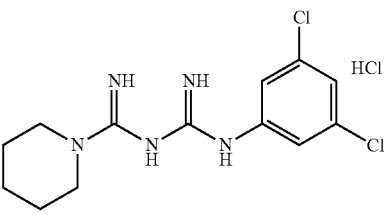 [SMILES: N=C(NC(=N)N1CCCCC1)Nc1cc(Cl)cc(Cl)c1 ; Cl]

¹H NMR (600 MHz, DMSO-d₆) δ 10.22 (br, s, 1H), 7.86 (br, s, 2H), 7.49 (s, 2H), 7.20 (s, 1H), 7.00 (br, s, 2H), 3.47 (m, 4H), 1.44 (m, 6H); LC-MS m/z 314.3[M+1]⁺; mp 230-231° C.

Example 62

N1-piperidine-N5-(2,4-dichloro)phenyl biguanide hydrochloride

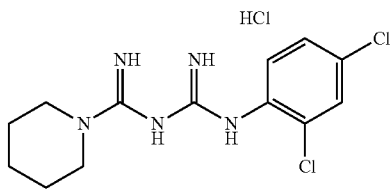 [SMILES: Cl ; N=C(NC(=N)N1CCCCC1)Nc1ccc(Cl)cc1Cl]

$^1$H NMR (600 MHz, DMSO-d$_6$) δ 8.90 (br, s, 1H), 7.74 (d, J=9.0 Hz, 1H), 7.73 (br, s, 2H), 7.63 (d, J=2.4 Hz, 1H), 7.39 (dd, J=9.0, 2.4 Hz, 1H), 7.20 (br, s, 2H), 3.39 (m, 4H), 1.56 (m, 2H), 1.51 (m, 4H); LC-MS m/z 314.0[M+1]$^+$; mp 262-263° C.

Example 63

N1-pyrrolidine-N5-(3,4-dichloro)phenyl biguanide hydrochloride

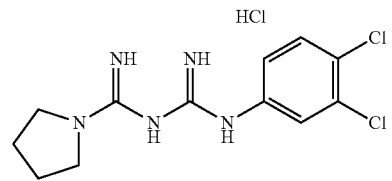 [SMILES: Cl ; N=C(NC(=N)N1CCCC1)Nc1ccc(Cl)c(Cl)c1]

$^1$H NMR (600 MHz, DMSO-d$_6$) δ 10.13 (br, s, 1H), 7.80 (d, J=3.0 Hz, 1H), 7.69 (br, s, 2H), 7.51 (d, J=9.0 Hz, 1H), 7.36 (dd, J=9.0, 3.0 Hz, 1H), 6.97 (br, s, 2H), 3.35 (m, 4H), 1.95 (m, 2H), 1.84 (m, 4H); LC-MS m/z 300.2[M+1]$^+$; mp 282-283° C.

Example 64

N1-piperidine-N5-(3,4-dichloro)phenyl biguanide hydrochloride

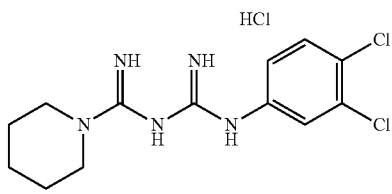 [SMILES: Cl ; N=C(NC(=N)N1CCCCC1)Nc1ccc(Cl)c(Cl)c1]

$^1$H NMR (600 MHz, DMSO-d$_6$) δ 10.12 (br, s, 1H), 7.80 (br, s, 2H), 7.74 (d, J=2.4 Hz, 1H), 7.05 (dd, J=8.4, 2.4 Hz, 1H), 7.28 (d, J=8.4 Hz, 1H), 6.95 (br, s, 2H), 3.40 (m, 4H), 1.54 (m, 6H); LC-MS m/z 314.2[M+1]$^+$; mp 267-269° C.

Example 65

N1-piperidine-N5-(3-chloro-5-trifluoromethoxy)phenyl biguanide hydrochloride

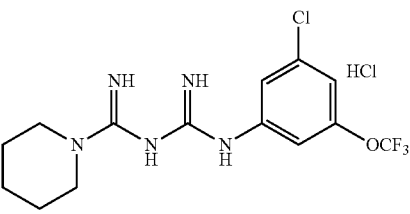 [SMILES: N=C(NC(=N)N1CCCCC1)Nc1cc(Cl)cc(OC(F)(F)F)c1 ; Cl]

$^1$H NMR (600 MHz, DMSO-d$_6$) δ 0.97 (br, s, 1H), 7.85 (br, s, 2H), 7.52 (s, 1H), 7.45 (s, 1H), 7.15 (s, 1H), 6.94 (br, s, 2H), 3.45 (m, 4H), 0.59 (m, 2H), 1.56 (m, 4H); LC-MS m/z 364.2[M+H]$^+$; mp 208-209° C.

Example 66

N1-pyrrolidine-N5-(3-bromo-5-trifluoromethoxy)phenyl biguanide hydrochloride

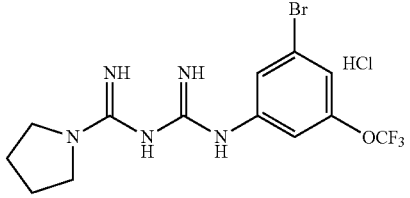 [SMILES: N=C(NC(=N)N1CCCC1)Nc1cc(Br)cc(OC(F)(F)F)c1 ; Cl]

$^1$H NMR (600 MHz, DMSO-d$_6$) δ 10.18 (br, s, 1H), 7.74 (br, s, 2H), 7.69 (s, 2H), 7.52 (s, 1H), 7.23 (s, 1H), 6.95 (br, s, 2H), 3.35 (m, 4H), 1.96 (m, 2H), 1.85 (m, 2H); LC-MS m/z 394.2[M+1]$^+$; mp 241-242° C.

Example 67

N1-piperidine-N5-(3-bromo-5-trifluoromethoxy)phenyl biguanide hydrochloride

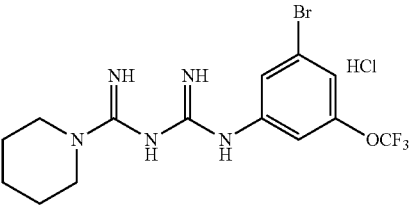 [SMILES: N=C(NC(=N)N1CCCCC1)Nc1cc(Br)cc(OC(F)(F)F)c1 ; Cl]

$^1$H NMR (600 MHz, DMSO-d$_6$) δ 10.03 (br, s, 1H), 7.85 (br, s, 2H), 7.65 (s, 1H), 7.50 (s, 1H), 7.26 (s, 1H), 6.96 (br, s, 2H), 3.45 (m, 4H), 1.60 (m, 2H), 1.55 (m, 4H); LC-MS m/z 408.0[M+H]$^+$; mp 205-207° C.

Example 68

N1-piperidine-N5-(3,4,5-trifluoro)phenyl biguanide hydrochloride

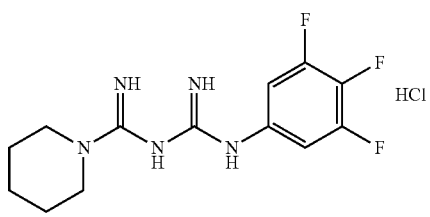 [SMILES: N=C(NC(=N)N1CCCCC1)Nc1cc(F)c(F)c(F)c1 ; Cl]

$^1$H NMR (600 MHz, DMSO-d$_6$) δ 10.38 (br, s, 1H), 7.88 (br, s, 2H), 7.34 (dd, J=10.2, 6.6 Hz, 2H), 6.97 (br, s, 2H), 3.45 (m, 4H), 1.57 (m, 6H); LC-MS m/z 300.2[M+1]$^+$; mp 248-249° C.

Example 69

N1-piperidine-N5-(2,4,6-trifluoro)phenyl biguanide hydrochloride

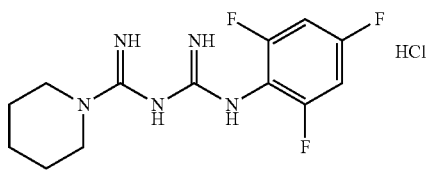 [SMILES: N=C(NC(=N)N1CCCCC1)Nc1c(F)cc(F)cc1F ; Cl]

$^1$H NMR (600 MHz, DMSO-d$_6$) δ 8.78 (br, s, 1H), 7.62 (br, s, 2H), 7.26 (dd, J=8.4, 8.4 Hz, 2H), 7.05 (br, s, 2H), 3.35 (m, 4H), 1.55 (m, 2H), 1.48 (m, 4H); LC-MS m/z 300.3 [M+1]$^+$; mp 243-244° C.

Example 70

N1-pyrrolidine-N5-(4-trifluoromethyl)phenyl biguanide acetate

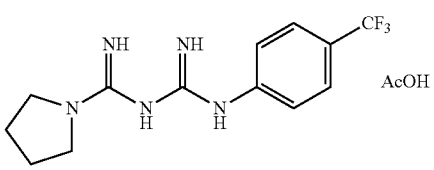 [SMILES: "AcOH" ; N=C(NC(=N)N1CCCC1)Nc1ccc(C(F)(F)F)cc1]

(1-1) Free base of N1-pyrrolidine-N5-(4-trifluoromethyl)phenyl biguanide

A solution obtained by dissolving Amberlyst®A26(OH) ion exchange resin (30 g) in methanol (20 ml) was stirred at room temperature for 10 minutes, and the ion exchange resin was then filled in a column (diameter: 3 cm, height: 80 cm). Thereafter, methanol (200 ml) was run through the column. A solution obtained by dissolving hydrochloride salt (2.82 g, 7.67 mmol) prepared in Example 26 in methanol (3 ml) was loaded into the column, and methanol (200 ml) was run through the column. The collected solution was concentrated under reduced pressure to obtain the white solid. Then, ethyl acetate (100 ml) was added to the white solid and stirred for 10 minutes. The resulting mixture was filtered and the filtrate was concentrated under reduced pressure to obtain a free base of N1-pyrrolidine-N5-(4-trifluoromethyl)phenyl biguanide as a white solid (2.37 g, 93%). The free base was used in subsequent operations without further purification.

Preparation of (1-2)N1-pyrrolidine-N5-(4-trifluoromethyl)phenyl biguanide acetate Acetic acid (0.614 ml, 10.7 mmol) was added to a solution obtained by dissolving the free base (2.37 g, 7.15 mmol) prepared in Operation (1-1) in methanol (10 ml) and stirred at room temperature for 30 minutes. The reaction mixture was concentrated under reduced pressure. Ethyl acetate (10 ml) was added to the concentrate and stirred at room temperature for 30 minutes. The formed solid was filtered to obtain a white solid target compound (2.43 g, 81%).

$^1$H NMR (600 MHz, CD$_3$OD) δ 7.61 (d, J=9.0 Hz, 2H), 7.57 (d, J=9.0 Hz, 2H), 3.51 (t, J=6.0 Hz, 2H), 3.43 (t, J=6.0 Hz, 2H), 2.07 (m, 2H), 1.94 (m, 2H), 1.90 (s, 3H); LC-MS m/z 300.2[M+1]$^+$; mp 202-204° C.

Target compounds of the following Examples 71 to 77 were prepared in the same manner as in Operations (1-1) and (1-2) of Example 70, except that the hydrochloride salts prepared in Examples 27, 32, 33, 48, 49, 53 and 54, which corresponds to the target compounds, were respectively used instead of the hydrochloride salt of Example 26 which was used in Operation (1-1) of Example 70.

Example 71

N1-piperidine-N5-(4-trifluoromethyl)phenyl biguanide acetate

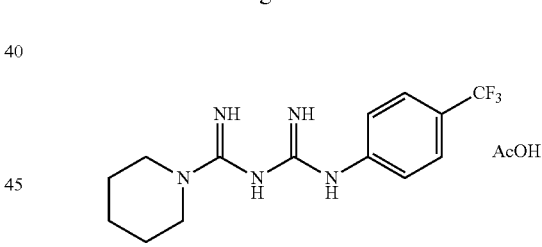

$^1$H NMR (600 MHz, CD$_3$OD) δ 7.58 (m, 4H), 3.54 (t, J=5.4 Hz, 4H), 1.89 (s, 3H), 1.71 (m, 2H), 1.66 (m, 4H); LC-MS m/z 314.3[M+1]$^+$; mp 198-200° C.

Example 72

N1-pyrrolidine-N5-(4-trifluoromethoxy)phenyl biguanide acetate

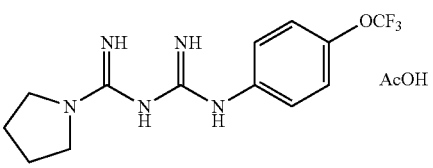 [SMILES: "AcOH" ; N=C(NC(=N)N1CCCC1)Nc1ccc(OC(F)(F)F)cc1]

¹H NMR (400 MHz, CD₃OD) δ 7.49 (d, J=8.8 Hz, 2H), 7.21 (d, J=8.8 Hz, 2H), 3.48 (m, 2H), 3.40 (m, 2H), 2.05 (m, 2H), 1.95 (m, 2H), 1.90 (s, 3H); LC-MS m/z 316.2[M+1]⁺; mp 196-198° C.

Example 73

N1-piperidine-N5-(4-trifluoromethoxy)phenyl biguanide acetate

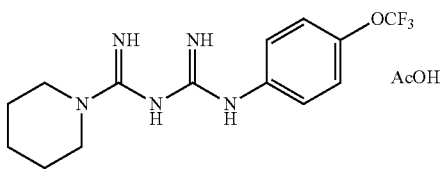 [SMILES: "AcOH" ; N=C(NC(=N)N1CCCCC1)Nc1ccc(OC(F)(F)F)cc1]

¹H NMR (600 MHz, CD₃OD) δ 7.45 (d, J=8.4 Hz, 2H), 7.22 (d, J=8.4 Hz, 2H), 3.52 (t, J=5.4 Hz, 4H), 1.89 (s, 3H), 1.69 (m, 2H), 1.64 (m, 4H); LC-MS m/z 330.2[M+1]⁺; mp 200-202° C.

Example 74

N1-pyrrolidine-N5-(3-fluoro-4-trifluoromethyl)phenyl biguanide acetate

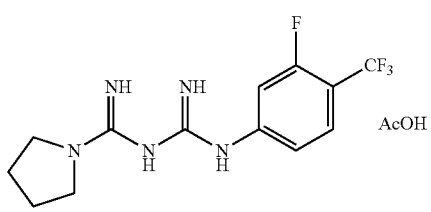 [SMILES: "AcOH" ; N=C(NC(=N)N1CCCC1)Nc1ccc(C(F)(F)F)c(F)c1]

¹H NMR (400 MHz, CD₃OD) δ 7.70 (d, J=13.2 Hz, 1H), 7.55 (dd, J=8.8, 8.8 Hz, 1H), 7.26 (d, J=8.8 Hz, 1H), 3.50 (m, 2H), 3.42 (m, 2H), 2.07 (m, 2H), 1.95 (m, 2H), 1.90 (s, 3H); LC-MS m/z 318.2[M+1]⁺; mp 204-205° C.

Example 75

N1-piperidine-N5-(3-fluoro-4-trifluoromethyl)phenyl biguanide acetate

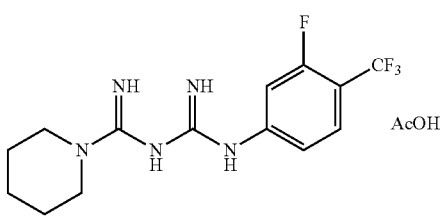 [SMILES: "AcOH" ; N=C(NC(=N)N1CCCCC1)Nc1ccc(C(F)(F)F)c(F)c1]

¹H NMR (600 MHz, CD₃OD) δ 7.63 (dd, J=13.2, 1.2 Hz, 1H), 7.56 (dd, J=7.8, 7.8 Hz, 1H), 7.25 (d, J=7.8 Hz, 1H), 3.55 (t, J=5.4 Hz, 4H), 1.90 (s, 3H), 1.72 (m, 2H), 1.67 (m, 4H); LC-MS m/z 332.2[M+1]⁺; mp 206-208° C.

Example 76

N1-pyrrolidine-N5-(3-fluoro-4-trifluoromethoxy)phenyl biguanide acetate

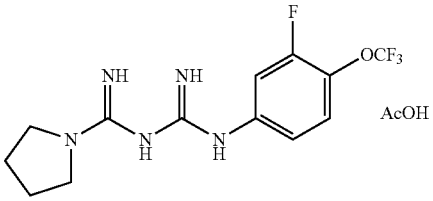 [SMILES: "AcOH" ; N=C(NC(=N)N1CCCC1)Nc1ccc(OC(F)(F)F)c(F)c1]

¹H NMR (600 MHz, CD₃OD) δ 7.62 (dd, J=12.6, 2.4 Hz, 1H), 7.32 (dd, J=9.0, 1.2 Hz, 1H), 7.17 (ddd, J=9.0, 2.4, 1.2 Hz, 1H), 3.49 (m, 2H), 3.42 (m, 2H), 2.06 (m, 2H), 1.96 (m, 2H), 1.90 (s, 3H); LC-MS m/z 334.1[M+1]⁺; mp 203-205° C.

Example 77

N1-piperidine-N5-(3-fluoro-4-trifluoromethoxy)phenyl biguanide acetate

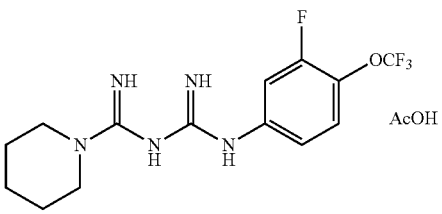 [SMILES: "AcOH" ; N=C(NC(=N)N1CCCCC1)Nc1ccc(OC(F)(F)F)c(F)c1]

¹H NMR (600 MHz, CD₃OD) δ 7.58 (dd, J=12.6, 2.4 Hz, 1H), 7.32 (d, J=9.0 Hz, 1H), 7.15 (ddd, J=9.0, 2.4, 1.2 Hz, 1H), 3.54 (t, J=5.4 Hz, 4H), 1.90 (s, 3H), 1.71 (m, 2H), 1.66 (m, 4H); LC-MS m/z 348.3[M+1]⁺; mp 202-204° C.

The solubilities in water of the hydrochlorides prepared in Examples 26, 27, 32, 33, 48, 49, 53 and 54, and the solubilities in water of the acetates prepared in Examples 70 to 77, were compared.

The experimental conditions and methods are described, as follows.

1) 1 ml of distilled water is added to a container including 5 mg of salt at room temperature.

2) The resulting mixture is stirred for 10 minutes, and then kept at room temperature for 1 hour.

3) Undissolved residual salt is recovered and weighed.

4) The ratio of the amount of the recovered salt and the amount of the dissolved salt is calculated.

5) Operations 1) to 4) are repeatedly performed with increasing amount (i.e., 10, 15, 20, 25 and 30 mg) of salt.

The experimental procedures were performed for each of the hydrochlorides of Examples 26, 27, 32, 33, 48, 49, 53 and 54 and the acetates of Examples 70 to 77. The comparative solubilities obtained using the hydrochlorides of Examples 26, 27, 32, 33, 48, 49, 53 and 54 and the acetates of Examples 70 to 77 are listed in the following Table 1.

TABLE 1

| Hydrochloride salt (mg/1 ml) | | Acetate salt(mg/1 ml) | | | | | |
|---|---|---|---|---|---|---|---|
| Content Examples | 5 | Content Examples | 5 | 10 | 15 | 20 | 25 30 |
| 26 | 80 | 70 | 100 | 100 | 100 | 100 | 100 50 |
| 27 | 20 | 71 | 100 | 50 | | | |
| 32 | 50 | 72 | 100 | 100 | 100 | 100 | 100 50 |
| 33 | 50 | 73 | 100 | 100 | 100 | 20 | |
| 48 | 80 | 74 | 100 | 100 | 100 | 50 | |
| 49 | 20 | 75 | 70 | | | | |
| 53 | 20 | 76 | 100 | 100 | 70 | | |
| 54 | 20 | 77 | 100 | 50 | | | |

Solubility in water (%)

From the results listed in Table 1, it can be seen that the solubilities in water of the acetates generally increased more than those of the hydrochlorides.

Experimental Examples

The compounds synthesized by the methods described in the examples of the present invention were evaluated for effects of AMPK activation and inhibition of cancer cell proliferation according to methods described in the following Experimental Examples.

Experimental Example 1

Measurement of AMPK Activation Effect

MCF7 cells derived from human breast cancer cells (commercially available from the Korean Cell Line Bank) were used, and the AMPK activation effect of the biguanide derivative was confirmed using an AMPKα immunoassay kit (Invitrogen, Catalog No. KHO0651).

MCF7 cells were cultured in a DMEM medium supplemented with 10% fetal bovine serum. Thereafter, the cultured MCF7 cells were put into a 6-well plate with approximately $5 \times 10^5$ cells per well and cultured in an incubator supplied with 5% $CO_2$. Culture media were treated with the derivatives synthesized in the examples at contents of 5, 10 and 50 μM, and then cultured for 24 hours. Metformin hydrochloride was used as the control, and the culture media were treated with 0.05, 0.5, 1, 2, 5 and 10 mM metformin hydrochloride, and then tested in the same manner as described in the derivatives synthesized in the examples. Subsequently, the cells were lysed according to a method presented in the operation manual of the AMPKα immunoassay kit, and 20 μg of a cell lysate was then yielded through protein assay. Thereafter, the AMPK activation effect was obtained by determining the degree of phosphorylation of $172^{nd}$ threonine residue (Thr172) of the AMPKα from the cell lysate according to the method presented in the operation manual of the AMPKα immunoassay kit. The degree of AMPK activation by the biguanide derivatives was exhibited as the degree of AMPKα phosphorylation in cells cultured in the presence of the compounds synthesized in the examples with respect to the degree of AMPKα phosphorylation in cells cultured without the treatment of the biguanide derivatives. A curve graph showing AMPK activation according to the concentration of the treated compounds was plotted based on the obtained AMPKα activation results, the concentration (activation concentration 150, AC150) value of the compound whose AMPK activation reached 150% was calculated using a GraphPad Prism 5.0 program, and the degrees of AMPK activation were obtained when concentrations of the treated biguanide derivatives were 10 μM and 50 μM and the metformin hydrochloride was 50 μM The results are listed in the following Table 2.

TABLE 2

| | AMPK activation effect | | |
|---|---|---|---|
| Example | AC150 (μM) | 10 μM (%) | 50 μM (%) |
| Metformin hydrochloride | 188.3 | | 130.0 |
| 7 | 0.9 | 526 | |
| 8 | 10.1 | | 347 |
| 9 | 12.4 | 149 | 255 |
| 10 | 7.3 | 178 | 598 |
| 11 | >50 | 127 | 127 |
| 12 | >50 | 107 | 149 |
| 13 | 16.0 | 97 | 300 |
| 14 | 4.0 | 204 | 429 |
| 15 | >50 | | 100 |
| 16 | 9.9 | | 378 |
| 17 | 8.4 | 167 | 512 |
| 18 | 3.4 | 281 | |
| 19 | 4.4 | 176 | 586 |
| 20 | 3.2 | 236 | 558 |
| 21 | 4.8 | 211 | 653 |
| 22 | 2.3 | 127 | 119 |
| 23 | 4.4 | 199 | 578 |
| 24 | 2.6 | 388 | |
| 25 | 46.6 | 99 | 156 |
| 26 | 3.1 | 255 | 642 |
| 27 | 2.4 | 455 | |
| 28 | 6.9 | 158 | 424 |
| 29 | 1.1 | 400 | |
| 30 | 6.4 | 187 | 636 |
| 31 | 15.3 | 145 | 232 |
| 32 | 5.1 | 204 | 680 |
| 33 | 1.4 | 538 | |
| 34 | 33.7 | 121 | 168 |
| 35 | 5.0 | 207 | 542 |
| 36 | 36.8 | 62 | 175 |
| 37 | 13.9 | 123 | 286 |
| 38 | >50 | 94 | 144 |
| 39 | >50 | 100 | 145 |
| 40 | >50 | 41 | 55 |
| 41 | >50 | 86 | 125 |
| 42 | >50 | 68 | 97 |
| 43 | 4.1 | 239 | 547 |
| 44 | >50 | 119 | 114 |
| 45 | 2.7 | 232 | 249 |
| 46 | 1.3 | 261 | |
| 47 | 7.3 | 169 | |
| 48 | 2.5 | 299 | |
| 49 | 2.7 | 258 | |
| 50 | >50 | 127 | |
| 51 | 7.8 | 160 | |
| 52 | 3.3 | 265 | 740 |
| 53 | 5.0 | 315 | |
| 54 | 0.5 | 400 | |
| 55 | 2.6 | 342 | |
| 56 | 2.0 | 367 | |
| 57 | 3.2 | 345 | |
| 58 | 16.5 | 131 | 265 |
| 59 | 3.6 | 269 | 1036 |
| 60 | 8.2 | 144 | 576 |
| 61 | 3.3 | 239 | |
| 62 | 5.6 | 208 | |
| 63 | 6.2 | 261 | |
| 64 | 0.7 | 442 | |
| 65 | 5.0 | | |
| 66 | 5.0 | 521 | |
| 67 | 5.0 | | |
| 68 | 7.2 | 197 | |
| 69 | 42.0 | 131 | 156 |
| 70 | 2.0 | 554 | |
| 71 | 2.3 | 313 | |
| 72 | 4.6 | 186 | 938 |
| 73 | 0.3 | 270 | 747 |

TABLE 2-continued

| | AMPK activation effect | | |
|---|---|---|---|
| Example | AC150 (μM) | 10 μM (%) | 50 μM (%) |
| 74 | 3.4 | 461 | |
| 75 | 2.0 | 710 | |
| 76 | 1.3 | 341 | |
| 77 | | | |

Experimental Example 2

Measurement of Effect of Inhibiting Cancer Cell Proliferation

HCT116 cells derived from human colorectal cancer (commercially available from the Korean Cell Line Bank) were used, and the effect of inhibiting cancer cell proliferation of the biguanide derivative was confirmed by measuring the concentration value (cell growth inhibition concentration, GIC50) at which cell growth was inhibited by 50% using a 3-(4,5-dimethylthiazol-2-yl)-2,5-diphenyltetrazolium bromide (MTT) reagent.

First, HCT116 cells were put on a 96-well plate and cultured in a DMEM medium containing 10% fetal bovine serum for 16 hours so that the cellcount in each well was approximately 5,000. Subsequently, to obtain the GIC50 value of each compound, culture media were treated with 100 μM, 25 μM, 6.25 μM, 1.56 μM or 0.39 μM of the compound, and then cultured for 48 hours. Metformin hydrochloride was used as the control, and the culture media were treated with 25, 12.5, 2.5, 0.5, 0.1 mM metformin hydrochloride, and then tested in the same manner as described in the derivatives synthesized in the examples. In order to determine whether the cells survived after treatment with the compounds, MTT was added to the culture media which were then cultured for another 3 hours. Formed formazane crystals were dissolved using dimethyl sulfoxide (DMSO), and the absorbance of the resulting solution was measured at 560 nm. After the 48-hour culture, the ratio of the cell count cultured on a well plate not treated with the compound to the living cell count on a well plate treated with the compounds synthesized in the examples was indicated as cell viability (%) according to each treated concentration. A cell viability curve graph was plotted and the concentration (GIC50) value of the compound at which the growth was inhibited by 50% was calculated to confirm the inhibition effect of cancer cell proliferation. Also, the cell growth viability (%) when the concentration of the treated biguanide derivative and the metformin hydrochloride as the control were 100 μM was shown.

The results of effects on cancer cell growth inhibition are listed in the following Table 3.

TABLE 3

| | Effect of inhibition on cancer cell growth | |
|---|---|---|
| Example | GI50 (μM) | Cell Growth Inhibition (%) at 100 μM |
| Metformin hydrochloride | 2846 | 1.8 |
| 7 | 7 | 97.2 |
| 8 | 56.8 | 77.6 |
| 9 | 13.4 | 79.1 |
| 10 | 27.3 | 97.4 |
| 11 | >100 | 29.7 |

TABLE 3-continued

| | Effect of inhibition on cancer cell growth | |
|---|---|---|
| Example | GI50 (μM) | Cell Growth Inhibition (%) at 100 μM |
| 12 | >100 | 17.6 |
| 13 | >100 | 45.4 |
| 14 | >100 | 49.7 |
| 15 | >100 | 39.5 |
| 16 | 72.4 | 67.2 |
| 17 | 48.2 | 97.4 |
| 18 | 17 | 97.7 |
| 19 | 55.9 | 74.0 |
| 20 | 48.2 | 97.5 |
| 21 | 41.5 | 97.0 |
| 22 | >100 | 44.5 |
| 23 | 38.9 | 97.6 |
| 24 | 6.9 | 97.6 |
| 25 | 27.6 | 96.3 |
| 26 | 22.7 | 97.6 |
| 27 | 6.7 | 97.7 |
| 28 | 19 | 97.6 |
| 29 | 5.9 | 98.0 |
| 30 | 33.7 | 97.9 |
| 31 | 22.9 | 96.5 |
| 32 | 23.6 | 97.6 |
| 33 | 7.9 | 97.9 |
| 34 | 47.3 | 98.0 |
| 35 | 46.7 | 76.5 |
| 36 | >100 | 43.6 |
| 37 | >100 | 32.2 |
| 38 | >100 | 0.0 |
| 39 | >100 | 25.5 |
| 40 | >100 | 0.9 |
| 41 | >100 | 18.8 |
| 42 | >100 | 23.2 |
| 43 | 37.1 | 98.0 |
| 44 | >100 | 32.6 |
| 45 | >100 | 41.3 |
| 46 | 5.6 | 97.0 |
| 47 | 1.9 | 96.7 |
| 48 | 9.3 | 100.6 |
| 49 | 5.2 | 96.5 |
| 50 | 3.9 | 97.0 |
| 51 | 1.9 | 96.3 |
| 52 | 19.8 | 100.6 |
| 53 | 7.6 | 100.7 |
| 54 | 4.5 | 96.4 |
| 55 | 7.3 | 100.6 |
| 56 | 4.6 | 100.7 |
| 57 | 2.6 | 96.3 |
| 58 | >100 | 37.4 |
| 59 | 28.1 | 97.8 |
| 60 | 48.2 | 97.6 |
| 61 | 7.1 | 97.7 |
| 62 | 11.6 | 97.2 |
| 63 | 8.7 | 97.6 |
| 64 | 6.4 | 100.8 |
| 65 | 3.6 | 97.3 |
| 66 | 6.8 | 97.6 |
| 67 | 2.9 | 97.1 |
| 68 | 13.8 | 97.6 |
| 69 | >100 | 21.5 |
| 70 | 5.2 | |
| 71 | 6.7 | |
| 72 | 23.6 | |
| 73 | 7.9 | |
| 74 | 9.3 | |
| 75 | 5.2 | |
| 76 | 7.6 | |
| 77 | 4.5 | |

Experimental Example 3

Measurement of Effect of Inhibiting Mammosphere Formation

The cancer stem cells refer to cancer cells that have self-regeneration or differentiation capacity which is characteristically innate to stem cells. Here, the cancer stem cells show resistance to conventional anticancer therapy and poor prognosis. Therefore, the biguanide derivative has an effect of inhibiting cancer recurrence by inhibiting formation and proliferation of cancer stem cells, especially, breast cancer stem cells (mammosphere). Accordingly, the effect of the biguanide derivative of inhibiting breast cancer stem cell (mammosphere) formation was measured in an MCF7 cell line derived from human breast cancer forming mammospheres, and simple experimental methods are described, as follows.

MCF7 cells derived from human breast cancer were cultured (culture temperature: 37° C., pH: 7.0 to 7.4) in a DMEM medium supplemented with 10% (v/v) fetal bovine serum (commercially available from Gibco Life Technologies (US)) so that the MCF7 cells could grow to approximately 80% confluency and used in an experiment to determine an ability to form mammospheres. After MCF7 cells were made to single cells and the number of cell was counted, MCF7 cells were put in to a 24-well plate at 2,000 cells/well. An ultralow attachment 24 well plate (Corning, Cat#3473) to which cells do not bond was used. Also, a culture media for forming mammospheres was prepared so that a serum-free DMEM/F12 medium could include 2% B27 (commercially available from Invitrogen), 20 ng/ml EGF (commercially available from Sigma), 5 μg/ml insulin (commercially available from Sigma) and 1 μg/ml hydrocortisone (commercially available from Sigma). Cells were cultured in a $CO_2$ incubator for 24 hours and treated with each of the compounds synthesized in the examples at contents of 0.1 μM, 1 μM, 5 μM and 10 μM. Then, the cultured cells were added to the culture media for forming mammospheres so that a final volume of the culture broth could be adjusted to 1 ml. The cells were treated with the same concentrations of phenformin hydrochloride as the control and cultured in a $CO_2$ incubator for 8 days. Thereafter, the mammosphere-forming efficiency and size of the cells were observed. After 8 days, the number of mammospheres having a size of 50 um or more was determined to calculate the mammosphere-forming efficiency (MFE (%)). The MFE (%) is calculated according to the following Equation 1.

$$MFE(\%) = \frac{\text{Number of Formed Mammospheres}}{\text{Initial Cell Count}} \times 100 \quad \text{Equation 1}$$

When the cells were cultured for 8 days, MFE (%) of the cells on a plate treated with the phenformin hydrochloride and the compounds synthesized in the examples was compared with MFE (%) of the cells on a plate that was not treated with the compounds. The results are listed as the mammosphere formation inhibition rate (%) in the following Table 4, and the mammosphere-forming efficiencies of the respective compounds are shown in FIG. 1.

TABLE 4

| Example | | 0 μM | 0.1 μM | 1 μM | 5 μM | 10 μM |
|---|---|---|---|---|---|---|
| Phenformin | Number of Mammospheres | 103 | 84 ± 2.8 | 79 ± 0.7 | 103 ± 1.4 | 116 ± 19.1 |
| hydrochloride | MFE (%) | 5.2 | 4.2 | 3.9 | 5.2 | 5.8 |
| | Inhibition rate (%) | 0.0 | 18.4 | 23.8 | 0 | −12.1 |
| 20 | Number of Mammospheres | 103 | 72 | 103 | 75 | 29 |
| | MFE (%) | 5.2 | 3.6 | 5.2 | 3.8 | 1.5 |
| | Inhibition (%) | 0.0 | 30.1 | 0 | 27.2 | 71.8 |
| 21 | Number of Mammospheres | 103 | 115 | 105 | 71 ± 4.2 | 46 ± 2.1 |
| | MFE (%) | 5.2 | 5.8 | 5.3 | 3.6 | 2.3 |
| | Inhibition (%) | 0.0 | 30.1 | −1.9 | 31.1 | 55.8 |
| 26 | Number of Mammospheres | 103 | 105 | 112 | 120 | 72 ± 11.3 |
| | MFE (%) | 5.2 | 5.3 | 5.6 | 6.0 | 3.6 |
| | Inhibition (%) | 0.0 | −11.7 | −8.7 | −16.5 | 30.1 |
| 27 | Number of Mammospheres | 103 | 103 | 105 ± 16.3 | 61 ± 3.5 | 32 |
| | MFE (%) | 5.2 | 5.2 | 5.2 | 3.0 | 1.6 |
| | Inhibition (%) | 0.0 | 0 | −1.5 | 41.3 | 68.9 |

Based on the experimental results, it could be confirmed that the compounds synthesized in the examples had an inhibitory effect on formation and proliferation of cancer stem cells.

Experimental Example 4

Confirmation of EMT Inhibitory Effect by Inhibition of Snail Expression

Cells undergoing EMT owing to various cytokines and growth factors can acquire motility and thus move a distance to form tumors in new tissues. Therefore, the metastasis of cancer cells can be inhibited by controlling expression of EMT-related transcription factors to hinder EMT. Based on these facts, the activities of biguanide derivatives that inhibit Snail expression, which is a transcription factor inducing EMT in the MCF7 cell line derived from human breast cancer, were measured and simple experimental methods are described, as follows.

Figure 2:
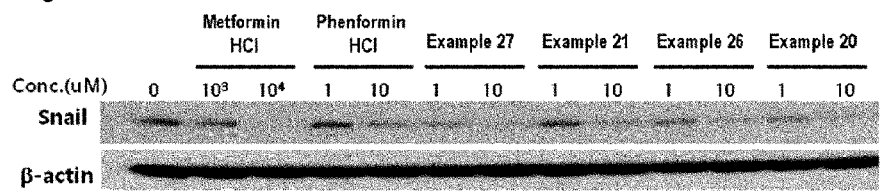
FIG. 2 shows the immunoblotting results showing a Snail expression inhibition effect of the compound of Formula 1 according to the present invention.

MCF7 cells derived from human breast cancer (commercially available from Korean Cell Line Bank) were cultured in a DMEM medium supplemented with 10% (v/v) fetal bovine serum (commercially available from Gibco Life Technologies (US)), put into a 6-well plate so that the number of cultured cells could amount to approximately $5 \times 10^5$ cells per well, and then incubated in an incubator supplied with 5% $CO_2$ (culture temperature: 37° C., pH: 7.0 to 7.4). The culture media were treated with phenformin hydrochloride and the compounds synthesized in the examples at contents of 1 μM and 10 μM, respectively, and then incubated for 48 hours. Metformin hydrochloride was used as the control, and the cells were treated with 1 mM and 10 mM metformin hydrochloride. After 48 hours, the cells were lysed in a cell lysis buffer containing 10 mM Tris HCl (pH7.4), 100 mM NaCl, 1 mM EDTA, 1 mM EGTA, 1 mM NaF, 20 mM $Na_4P_2O_7$, 2 mM $Na_3VO_4$, 1% TritonX-100, 10% glycerol, 0.5% deoxycholate and 1 mM PMSF. Then, 25 μg of the cell lysate was electrophoresized in an SDS-PAGE gel, and then transferred to a PMSF membrane (commercially available from Amersham Life Science). The membrane reacted with rat monoclonal anti-human Snail (commercially available from Cell signaling Technology) or mouse monoclonal anti-β-actin (commercially available from Santa cruz Biotechnology), and unbound antibodies were removed. In this case, anti-β-actin was used as the antibody to ensure that the amount of proteins loaded into the SDS-PAGE gel is identical. The membrane was reacted again with a secondary antibody, anti-rat IgG (commercially available from Cell signaling Technology) or anti-mouse IgG (commercially available from Santa Cruz Biotechnology). Finally, the antibody bound to the membrane was detected using an ECL Plus system (commercially available from Amersham Life Science). The results are shown in FIG. 2. Also, the expression level of Snail with respect to β-actin was analyzed using a Scion image analysis program. Here, when it was assumed that the expression level of the untreated control was 100%, the expression level of the Snail by treatment with the compounds synthesized in the examples was indicated as a percentage (%). The results are listed in the following Table 5.

TABLE 5

Results of Snail Expression Rate (%)

| Example | 0 | 1 mM | 10 mM |
|---|---|---|---|
| Metformin hydrochloride | 100% | 70.3 % | 13.6% |
| Examples | 0 | 1 μM | 10 μM |
| Phenformin hydrochloride | 100% | 117.6% | 53.8% |
| 20 | 100% | 57.6% | 8.7% |
| 21 | 100% | 83.5% | 29.8% |
| 26 | 100% | 57.2% | 14.6% |
| 27 | 100% | 52.7% | 13.2% |

Therefore, the compounds synthesized in the examples were considered to hinder EMT by inhibiting Snail expression, and also have the effect of inhibiting cancer metastasis.

The invention claimed is:

1. A compound of Formula 1 or a pharmaceutically acceptable salt thereof:

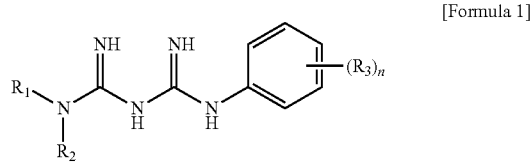

[Formula 1]

wherein R1 and R2 are taken together with nitrogen to which they are attached to form 3- to 8-membered heterocycloalkyl, wherein the heterocycloalkyl is unsubstituted or substituted with at least one substituent selected from the group consisting of halogen, hydroxy and C1-6alkyl;
n is an integer ranging from 2 to 5;
each R3 is unsubstituted or substituted and is independently selected from the group consisting of halogen, unsubstituted hydroxy, substituted C1-6alkyl, unsubstituted or substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl,
wherein the substituted R3 has at least one substituent selected from the group consisting of halogen, hydroxy and C1-6alkyl.

2. The compound of Formula 1 or the pharmaceutically acceptable salt thereof of claim 1,
wherein R1 and R2 are taken together with nitrogen to which they are attached to form 4- to 7-membered heterocycloalkyl, wherein the heterocycloalkyl is unsubstituted or substituted with at least one substituent selected from the group consisting of halogen, hydroxy and C1-6alkyl;
n is an integer ranging from 2 to 5;
each R3 is unsubstituted or substituted and is independently selected from the group consisting of halogen, unsubstituted hydroxy, substituted C1-6alkyl, unsubstituted or substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl,
wherein the substituted R3 has at least one substituent selected from the group consisting of halogen, hydroxy and C1-6alkyl.

3. The compound of Formula 1 or the pharmaceutically acceptable salt thereof of claim 1,
wherein R1 and R2 are taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl, wherein the heterocycloalkyl is unsubstituted or substituted with at least one substituent selected from the group consisting of halogen, hydroxy and C1-6alkyl;
n is an integer ranging from 2 to 5;
each R3 is unsubstituted or substituted and is independently selected from the group consisting of halogen, unsubstituted hydroxy, substituted C1-6alkyl, unsubstituted or substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl,
wherein the substituted R3 has at least one substituent selected from the group consisting of halogen, hydroxy and C1-6alkyl.

4. The compound of Formula 1 or the pharmaceutically acceptable salt thereof of claim 1,
wherein R1 and R2 are taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl, wherein the heterocycloalkyl is unsubstituted or substituted with at least one substituent selected from the group consisting of halogen, hydroxy and C1-6alkyl;
n is an integer ranging from 2 to 3;
each R3 is unsubstituted or substituted and is independently selected from the group consisting of halogen, unsubstituted hydroxy, substituted C1-6alkyl, unsubstituted or substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl, wherein the substituted R3 has at least one substituent selected from the group consisting of halogen, hydroxy and C1-6alkyl.

5. The compound of Formula 1 or the pharmaceutically acceptable salt thereof of claim 1, wherein R1 and R2 are taken together with nitrogen to which they are attached to form 4- to 7-membered heterocycloalkyl selected from the group consisting of azetidinyl, pyrrolidinyl, piperidinyl, morpholinyl, piperazinyl and azepanyl, wherein the heterocycloalkyl is unsubstituted or substituted with at least one substituent selected from the group consisting of halogen, hydroxy and C1-6alkyl; and n is an integer ranging from 2 to 3;

each R3 is unsubstituted or substituted and is independently selected from the group consisting of halogen, unsubstituted hydroxy, substituted C1-6alkyl, unsubstituted or substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl, wherein the substituted R3 has at least one substituent selected from the group consisting of halogen, hydroxy and C1-6alkyl.

6. The compound of Formula 1 or the pharmaceutically acceptable salt thereof of claim 1, wherein R1 and R2 are taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl, wherein the piperazinyl is substituted with C1-6alkyl;

n is an integer ranging from 2 to 3; and each R3 is unsubstituted or substituted and is independently selected from the group consisting of halogen, unsubstituted hydroxy, substituted C1-6alkyl, unsubstituted or substituted C1-6alkoxy, unsubstituted or substituted C1-6alkylthio, unsubstituted or substituted amino, unsubstituted or substituted amide, unsubstituted or substituted sulfonamide, nitro, heteroaryl, cyano, sulfonic acid and unsubstitutedd or substituted sulfamoyl, wherein the substituted C1-6alkyl or substituted C1-6alkoxy are each independently substituted with halogen or hydrin, the substituted amino is substituted with C1-C6alkkyl, the substituted amide is acetamide, the suhstilutcd sulfonamide is alkylsulfonamide, and the heteroryl is tetrazoyl.

7. The compound of Formula 1 or the pharmaceutically acceptable salt thereof of claim 1, wherein R1 and R2 are taken together with nitrogen to which they are attached to form pyrrolidinyl or piperidinyl;

n is 2; and each R3 is independently selected from the group consisting of halogen, C1-6haloalkyl and C1-6haloalkoxy.

8. The compound of Formula 1 or the pharmaceutically acceptable salt thereof of claim 1, wherein the compound of Formula 1 is N1-piperidine-N5-(3,5-dimethoxy)phenyl biguanide;
N1-piperidine-N5-(4-fluoro-3-trifluoromethyl)phenyl biguanide;
N1-piperidine-N5-(4-chloro-3-trifluoromethyl)phenyl biguanide;
N1-pyrrolidine-N5-(3-fluoro-4-trifluoromethyl)phenyl biguanide;
N1-piperidine-N5-(3-fluoro-4-trifluoromethyl)phenyl biguanide;
N1-piperidine-N5-(4-fluoro-3-trifluoromethoxy)phenyl biguanide;
N1-piperidine-N5-(4-chloro-3-trifluoromethoxy)phenyl biguanide;
N1-azetidine-N5-(3-fluoro-4-trifluoromethoxy)phenyl biguanide;
N1-pyrrolidine-N5-(3-fluoro-4-trifluoromethoxy)phenyl biguanide;
N1-piperidine-N5-(3-fluoro-4-trifluoromethoxy)phenyl biguanide;
N1-azetidine-N5-(3-chloro-4-trifluoromethoxy)phenyl biguanide;
N1-pyrrolidine-N5-(3-chloro-4-trifluoromethoxy)phenyl biguanide;
N1-piperidine-N5-(3-chloro-4-trifluoromethoxy)phenyl biguanide;
N1-piperidine-N5-(2,4-difluoro)phenyl biguanide;
N1-piperidine-N5-(3,4-difluoro)phenyl biguanide;
N1-piperidine-N5-(3,5-difluoro)phenyl biguanide;
N1-piperidine-N5-(3,5-dichloro)phenyl biguanide;
N1-piperidine-N5-(2,4-dichloro)phenyl biguanide;
N1-pyrrolidine-N5-(3,4-dichloro)phenyl biguanide;
N1-piperidine-N5-(3,4-dichloro)phenyl biguanide;
N1-piperidine-N5-(3-chloro-5-trifluoromethoxy)phenyl biguanide;
N1-pyrrolidine-N5-(3-bromo-5-trifluoromethoxy)phenyl biguanide;
N1-piperidine-N5-(3-bromo-5-trifluoromethoxy)phenyl biguanide;
N1-piperidine-N5-(3,4,5-trifluoro)phenyl biguanide; or
N1-piperidine-N5-(2,4,6-trifluoro)phenyl biguanide.

9. The compound of Formula 1 or the pharmaceutically acceptable salt thereof of claim 1, wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid.

10. A method of preparing a compound of Formula 1, comprising:

reacting a compound of Formula 2 with dicyanoamide in an organic solvent to obtain a compound of Formula 3; and reacting the compound of Formula 3 with a compound of Formula 4 in water, an organic solvent or a mixture thereof to obtain the compound of Formula 1:

[Formula 1]

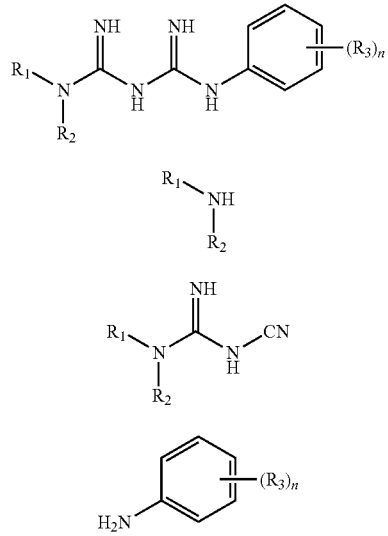

[Formula 2]

[Formula 3]

[Formula 4]

wherein R1 and R2 are taken together with nitrogen to which they are attached to form 3- to 8-membered heterocycloalkyl, wherein the heterocycloalkyl is unsubstituted or substituted with at least one substituent selected from the group consisting of halogen, hydroxy and C1-6alkyl;

n is an integer ranging from 2 to 5;

each R3 is unsubstituted or substituted and is independently selected from the group consisting of halogen, unsubstituted hydroxy, substituted C1-6alkyl, unsubstituted or substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl, wherein the substituted R3 has at least one substituent selected from the group consisting of halogen, hydroxy and C1-6alkyl.

11. A method of treating a disease comprising:
administering a therapeutically effective amount of a compound of Formula 1 or a pharmaceutically acceptable salt thereof defined in claim 1 to a subject suffering from the disease, wherein the disease is selected from the group consisting of diabetes mellitus, obesity, hyperlipemia, hypercholesterolemia, fatty liver, coronary artery disease, polycystic ovary syndrome, metabolic syndrome, breast cancer and colorectal cancer.

12. The method of claim 11, wherein the diabetes mellitus is insulin-in dependent diabetes mellitus.

13. The method of claim 11, wherein the treatment of the breast cancer and colorectal cancer includes inhibition of recurrence or metastasis of cancer.

14. A compound of Formula 1 or a pharmaceutically acceptable salt thereof:

[Formula 1]

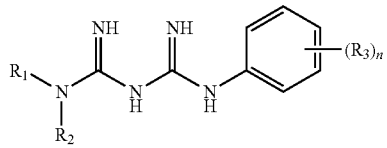

wherein R1 and R2 are taken together with nitrogen to which they are attached to form 3- to 8-membered heterocycloalkyl selected from the group consisting of azetidinyl, pyrrolidinyl, piperidinyl, piperazinyl, azepanyl and aziridinyl, wherein the heterocycloalkyl is unsubstituted or substituted with at least one substituent selected from the group consisting of halogen, hydroxy and C1-6alkyl;

n is 1;

each R3 is unsubstituted or substituted and is independently selected from the group consisting of unsubstituted hydroxy, substituted C1-6alkyl, substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl, and wherein the substituted R3 has at least one substituent selected from the group consisting of halogen, hydroxy and C1-6alkyl.

15. The compound of Formula 1 or the pharmaceutically acceptable salt thereof of claim 14, wherein R1 and R2 are taken together with nitrogen to which they are attached to form 4- to 7-membered heterocycloalkyl selected from the group consisting of azetidinyl, pyrrolidinyl, piperidinyl, piperazinyl, azepanyl and aziridinyl, wherein the heterocycloalkyl is unsubstituted or substituted with at least one substituent selected from the group consisting of halogen, hydroxy and C1-6alkyl;

n is 1;

each R3 is unsubstituted or substituted and is independently selected from the group consisting of unsubstituted hydroxy, substituted C1-6alkyl, substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl, and wherein the substituted R3 has at least one substituent selected from the group consisting of halogen, hydroxy and C1-6alkyl.

16. The compound of Formula 1 or the pharmaceutically acceptable salt thereof of claim 14,
wherein the compound of Formula 1 is
N1-piperidine-N5-(3-hydroxy)phenyl biguanide;
N1-piperidine-N5-(3-hydroxymethyl)phenyl biguanide;
N1-pyrrolidine-N5-(3-trifluoromethyl)phenyl biguanide;
N1-piperidine-N5-(3-trifluoromethyl)phenyl biguanide;
N1-azetidine-N5-(4-trifluoromethyl)phenyl biguanide;
N1-pyrrolidine-N5-(4-trifluoromethyl)phenyl biguanide;
N1-piperidine-N5-(4-trifluoromethyl)phenyl biguanide;
N1-pyrrolidine-N5-(3-trifluoromethoxy)phenyl biguanide;
N1-piperidine-N5-(3-trifluoromethoxy)phenyl biguanide;
N1-piperidine-N5-(3-difluoromethoxy)phenyl biguanide;
N1-azetidine-N5-(4-trifluoromethoxy)phenyl biguanide;

N1-pyrrolidine-N5-(4-trifluoromethoxy)phenyl biguanide;

N1-piperidine-N5-(4-trifluoromethoxy)phenyl biguanide;

N1-(4-methyl)piperazine-N5-(4-trifluoromethoxy)phenyl biguanide;

N1-piperidine-N5-(3-amino)phenyl biguanide;

N1-piperidine-N5-(4-dimethylamino)phenyl biguanide;

N1-piperidine-N5-(4-acetamide)phenyl biguanide;

N1-piperidine-N5-(3-acetamide)phenyl biguanide;

N1-piperidine-N5-(4-(1H-tetrazole-5-yl))phenyl biguanide;

N1-piperidine-N5-(3-methylsulfonamide)phenyl biguanide;

N1-piperidine-N5-(4-sulfonic acid)phenyl biguanide;

N1-piperidine-N5-(4-methylthio)phenyl biguanide; or

N1-piperidine-N5-(4-sulfamoyl)phenyl biguanide.

17. The compound of Formula 1 or the pharmaceutically acceptable salt thereof of claim 14, wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid.

18. The compound of Formula 1 or the pharmaceutically acceptable salt thereof of claim 14, wherein the compound of Formula 1 is N1-piperidine-N5-(4-trifluoromethyl)phenyl biguanide.

19. The compound of Formula 1 or the pharmaceutically acceptable salt thereof of claim 14, wherein the compound of Formula 1 is N1-pyrrolidine-N5-(4-trifluoromethoxy)phenyl biguanide.

20. A compound of Formula 1 or a pharmaceutically acceptable salt thereof:

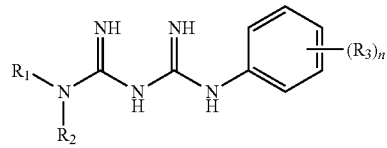

[Formula 1]

wherein R1 and R2 are taken together with nitrogen to which they are attached to form morpholinyl unsubstituted or substituted with at least one substituent selected from the group consisting of halogen, hydroxy and C1-6alkyl;

n is 1;

each R3 is unsubstituted or substituted and is independently selected from the group consisting of halogen, unsubstituted hydroxy, unsubstituted or substituted C1-6alkoxy, unsubstituted or substituted C1-6alkylthio, unsubstituted or substituted amino, unsubstituted or substituted amide, unsubstituted or substituted sulfonamide, nitro, unsubstituted or substituted heteroaryl, cyano, sulfonic acid and unsubstituted or substituted sulfamoyl, wherein the substituted R3 has at least one substituent selected from the group consisting of halogen, hydroxy and C1-6alkyl.

21. The compound of Formula 1 or the pharmaceutically acceptable salt thereof of claim 20, wherein the compound of Formula 1 is
N1-morpholine-N5-(3-bromo)phenyl biguanide; or
N1-morpholine-N5-(4-trifluoromethoxy)phenyl biguanide.

22. The compound of Formula 1 or the pharmaceutically acceptable salt thereof of claim 20, wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid.

* * * * *